United States Patent
Huang et al.

(10) Patent No.: US 10,330,919 B2
(45) Date of Patent: Jun. 25, 2019

(54) AM-EWOD DEVICE AND CONTROL METHODS WITH INTERMITTENT ACTUATION PATTERNS

(71) Applicant: Sharp Microfluidic Solutions Limited, Oxford (GB)

(72) Inventors: Laura Huang, Oxford (GB); Tim Boyle, Oxford (GB)

(73) Assignee: Sharp Life Science (EU) Limited, Oxford (GB)

( * ) Notice: Subject to any disclaimer, the term of this patent is extended or adjusted under 35 U.S.C. 154(b) by 152 days.

(21) Appl. No.: 15/475,410

(22) Filed: Mar. 31, 2017

(65) Prior Publication Data

US 2018/0284423 A1    Oct. 4, 2018

(51) Int. Cl.
| | | |
|---|---|---|
| *G02B 26/00* | (2006.01) | |
| *B01L 3/00* | (2006.01) | |
| *H01L 27/12* | (2006.01) | |

(52) U.S. Cl.
CPC ...... *G02B 26/005* (2013.01); *B01L 3/502792* (2013.01); *H01L 27/1214* (2013.01); *B01L 2200/0626* (2013.01); *B01L 2200/143* (2013.01); *B01L 2300/0663* (2013.01); *B01L 2300/161* (2013.01); *B01L 2400/0427* (2013.01)

(58) Field of Classification Search
CPC .................. G02B 26/005; B01L 3/50273
USPC ................. 359/290; 204/451, 600
See application file for complete search history.

(56) References Cited

U.S. PATENT DOCUMENTS

| | | |
|---|---|---|
| 6,565,727 B1 | 5/2003 | Shenderov |
| 6,911,132 B2 | 6/2005 | Pamula et al. |
| 7,163,612 B2 | 1/2007 | Sterling et al. |
| 7,569,129 B2 | 8/2009 | Pamula et al. |

(Continued)

FOREIGN PATENT DOCUMENTS

| | | |
|---|---|---|
| EP | 2741120 | 6/2014 |
| EP | 2884272 | 6/2015 |

(Continued)

OTHER PUBLICATIONS

"Digital microfluidics: is a true lab-on-a-chip possible?", R.B. Fair, Microfluid Nanofluid (2007) 3:245-281).

*Primary Examiner* — Kristina M Deherrera
(74) *Attorney, Agent, or Firm* — Renner, Otto, Boisselle & Sklar, LLP

(57) ABSTRACT

A microfluidic system includes an electro-wetting on dielectric (EWOD) device and a control system that controls actuation voltages applied to the element array of the EWOD device to perform manipulation operations as to fluid droplets. The control system applies a sequence of actuation voltages to a portion of the array elements associated with a droplet to maintain the droplet in a desired droplet state corresponding to a predetermined droplet property. The sequence of actuation voltages includes an actuation-on period in which the portion of the array elements associated with the droplet is actuated and an actuation-off period in which the portion of the array elements associated with the droplet is not actuated, and the actuation-off period is non-zero. The control system may apply a sequence of actuation voltages comprising a predetermined duty cycle, and/or the actuation voltages may be applied in accordance with a sensor based intervention.

20 Claims, 16 Drawing Sheets

(56) References Cited

U.S. PATENT DOCUMENTS

| | | | |
|---|---|---|---|
| 8,637,317 B2 * | 1/2014 | Pamula | B01F 11/0071 422/502 |
| 8,653,832 B2 | 2/2014 | Hadwen et al. | |
| 2010/0194408 A1 | 8/2010 | Sturmer et al. | |
| 2015/0021182 A1 | 1/2015 | Rival et al. | |
| 2015/0174578 A1 | 6/2015 | Srinivasan et al. | |

FOREIGN PATENT DOCUMENTS

| | | |
|---|---|---|
| JP | 2006500596 | 1/2006 |
| JP | 2007508584 | 4/2007 |
| JP | 2011508224 | 3/2011 |
| WO | WO 2008055256 A3 | 5/2008 |

* cited by examiner

Fig. 5
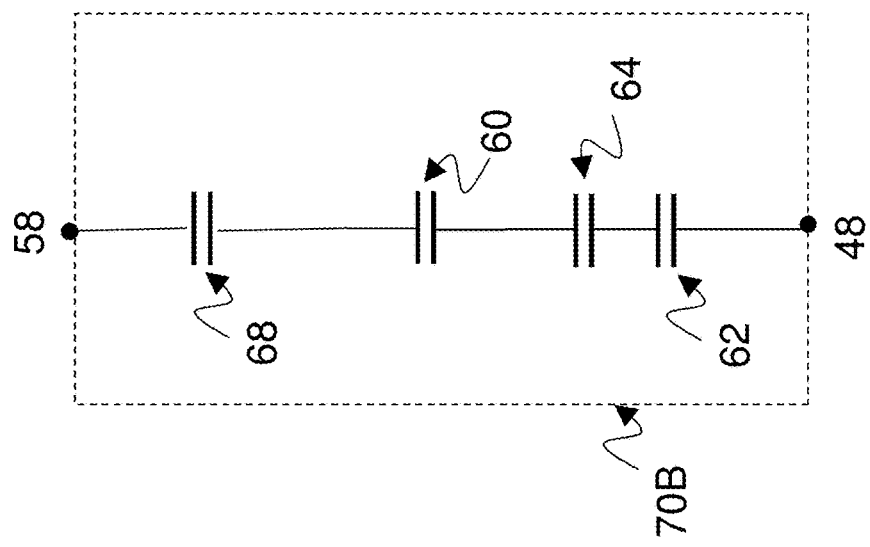
Figure 5A
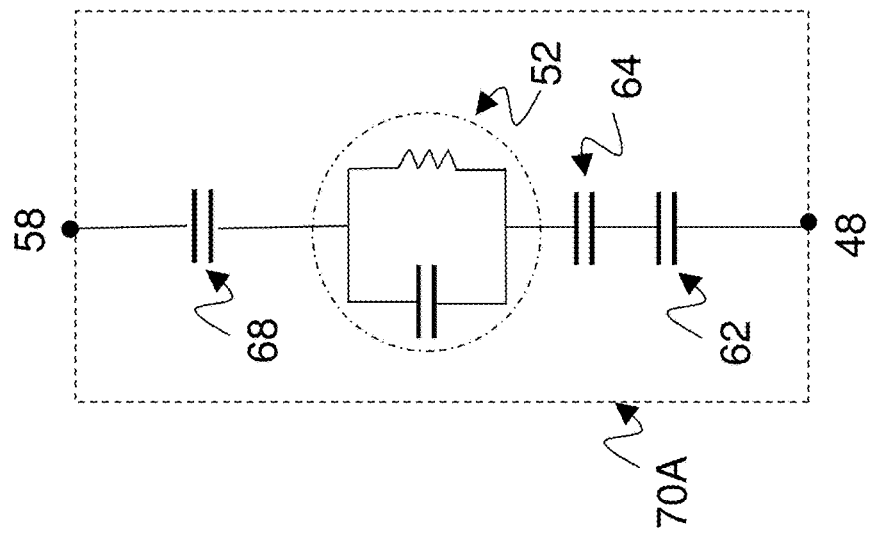
Figure 5B

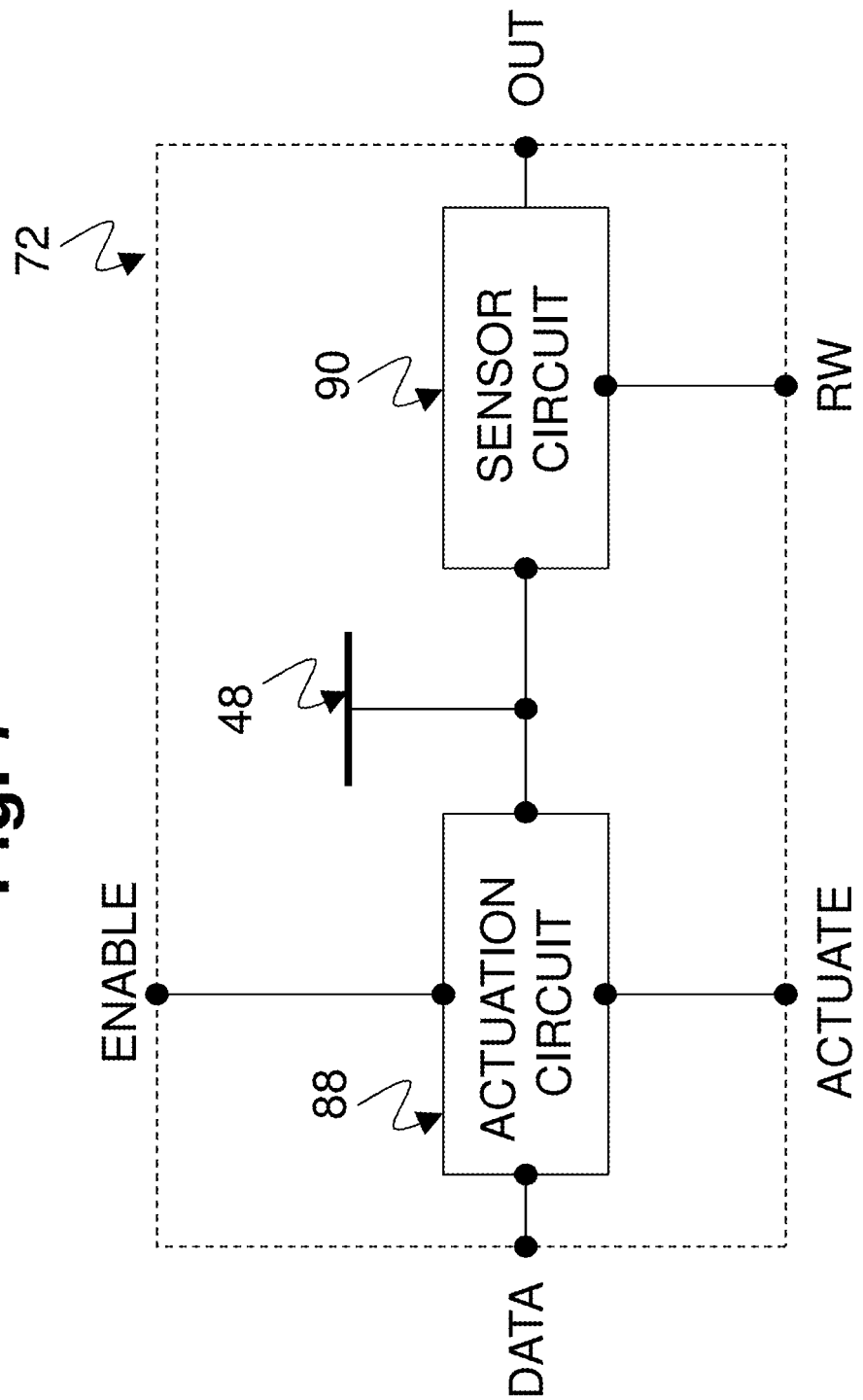

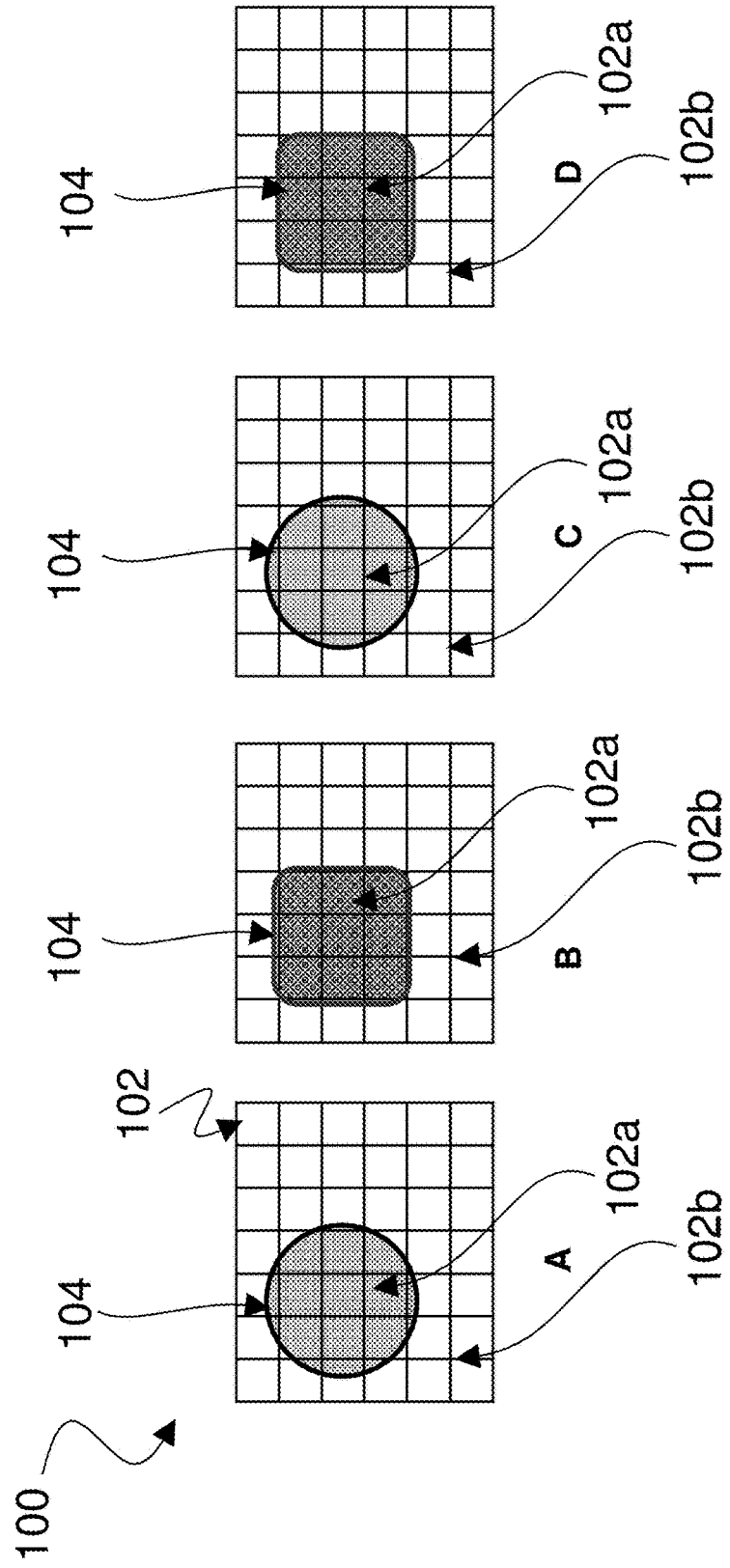

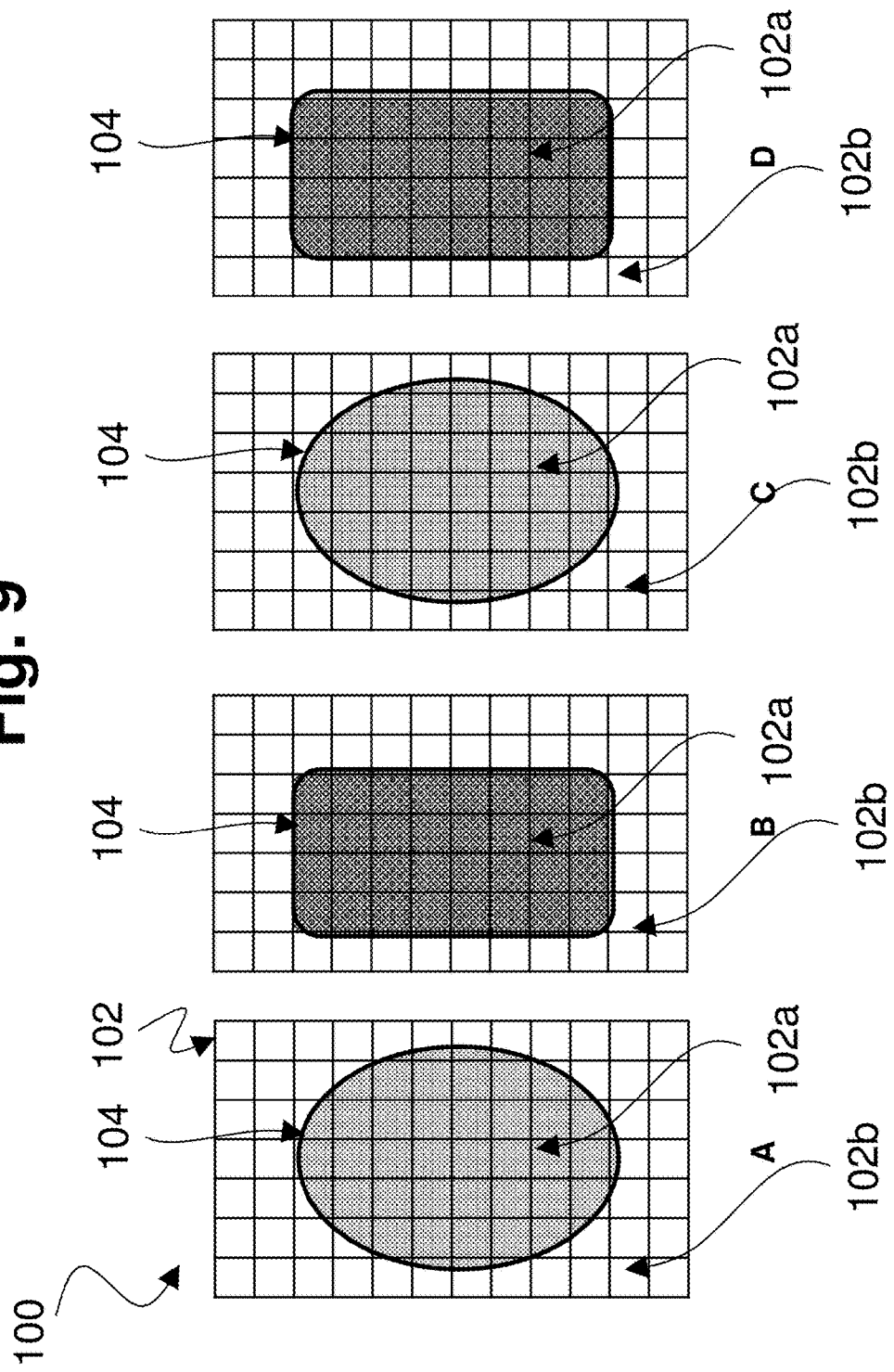

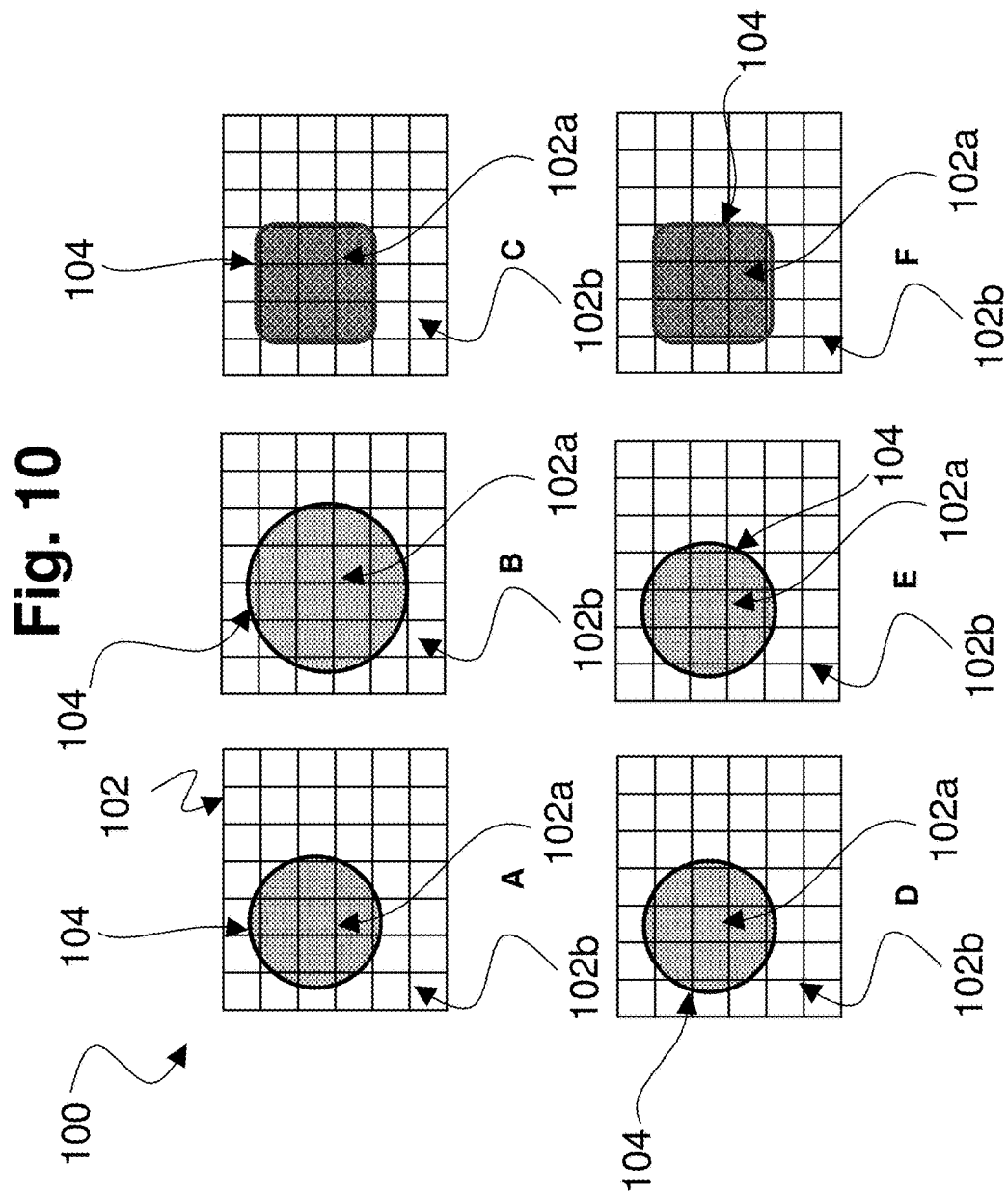

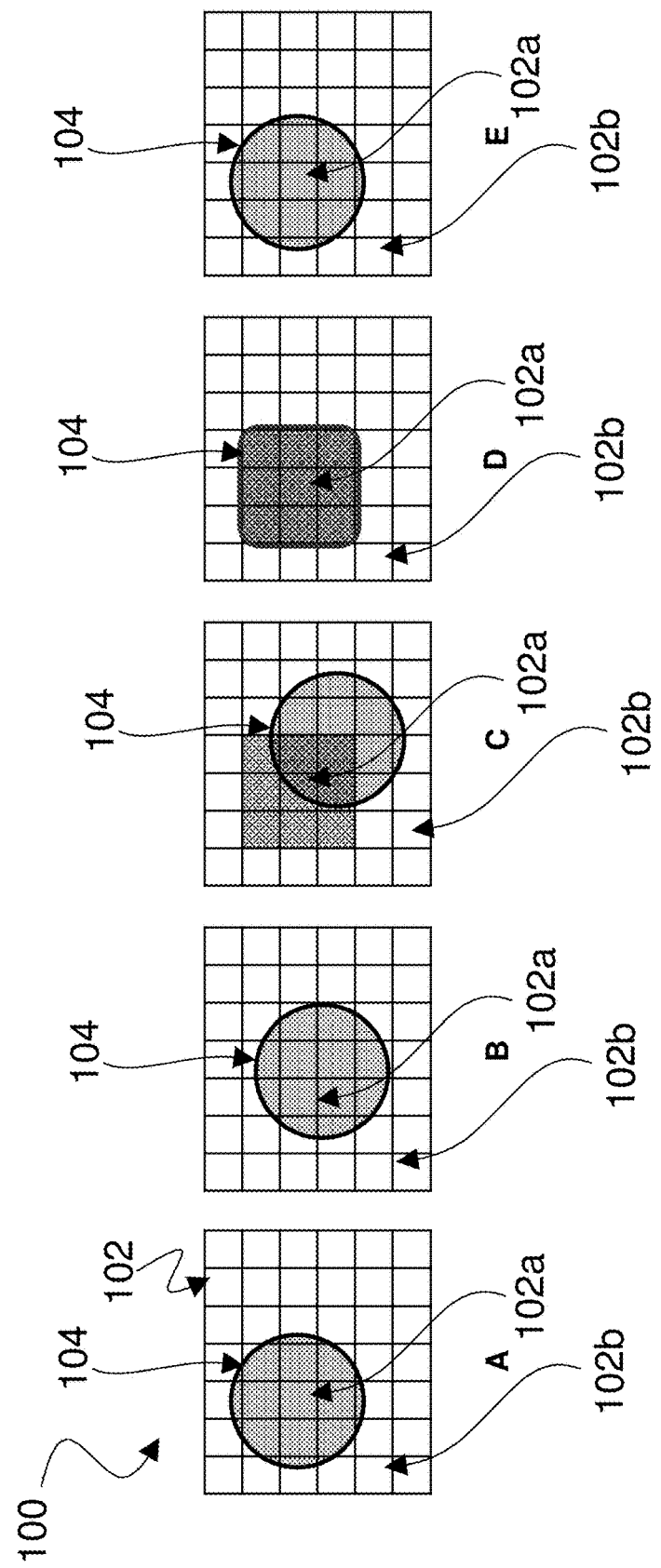

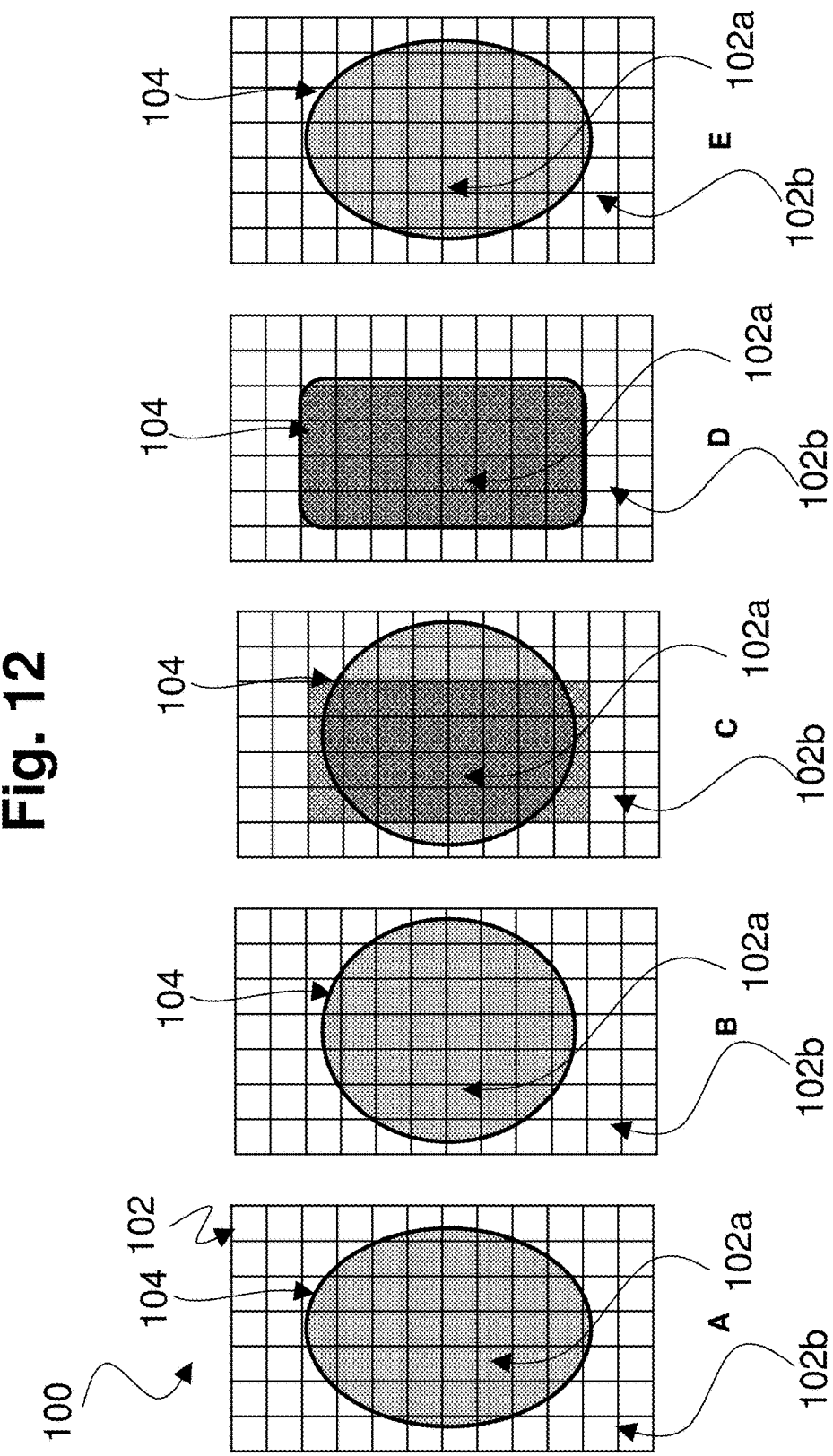

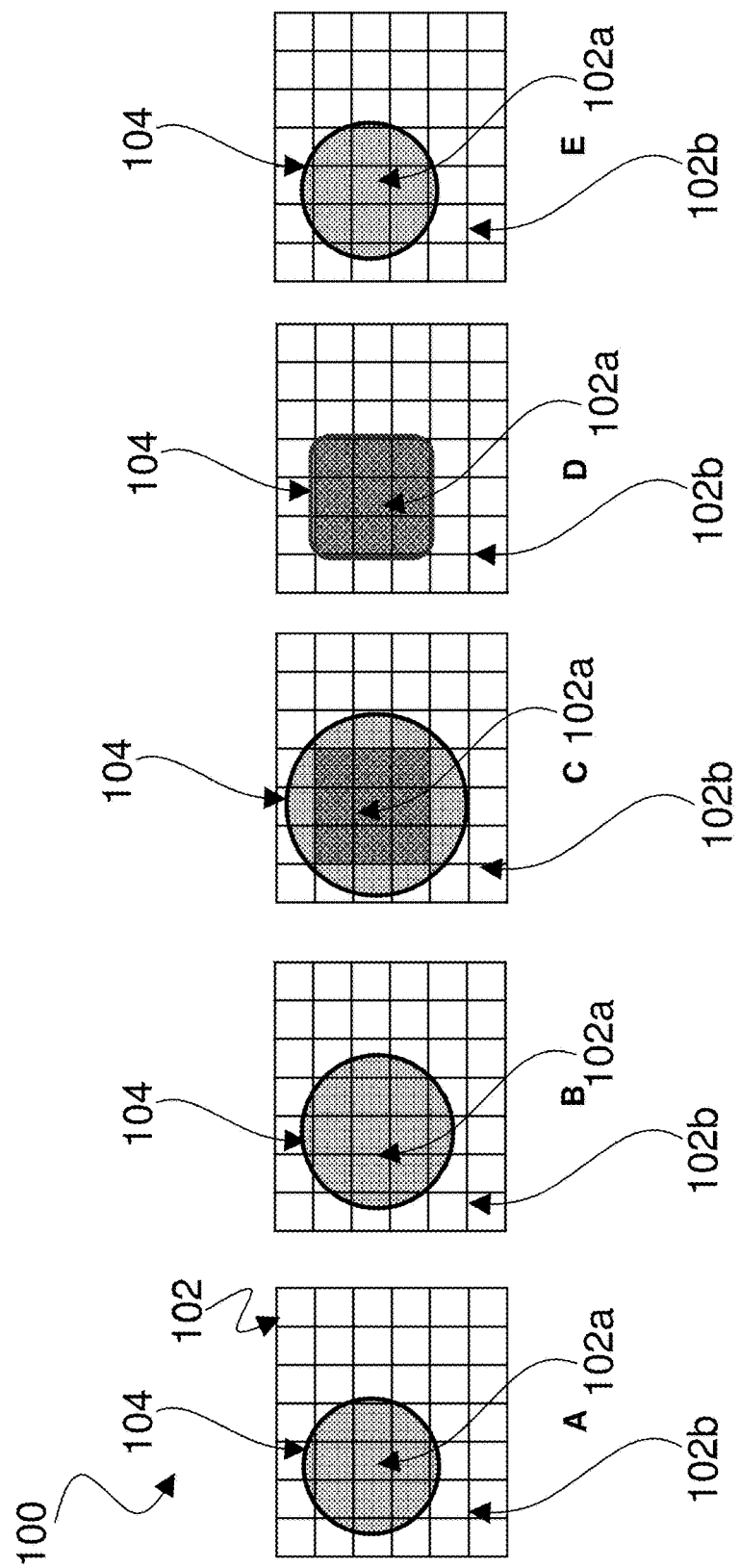

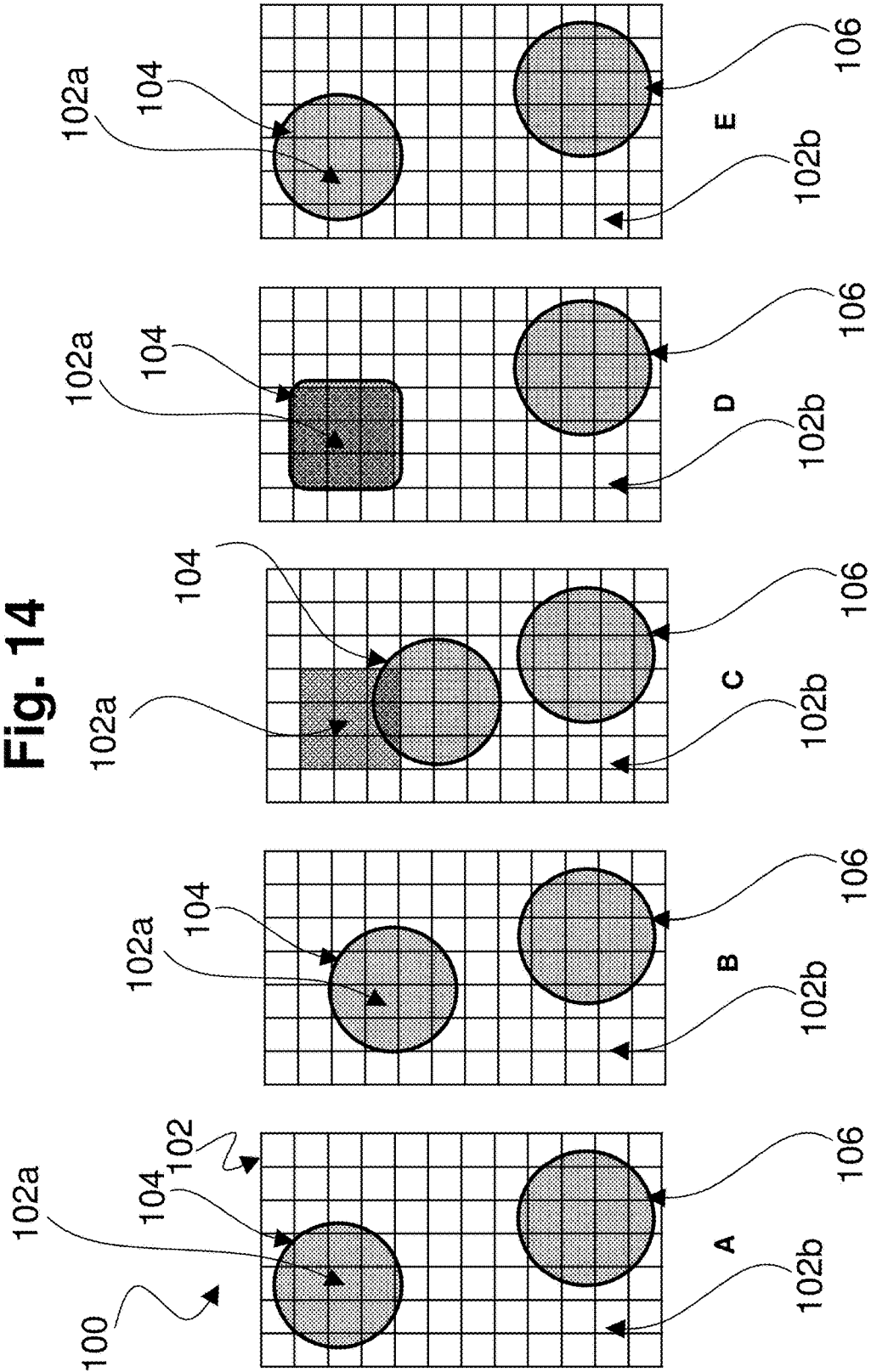

AM-EWOD DEVICE AND CONTROL METHODS WITH INTERMITTENT ACTUATION PATTERNS

TECHNICAL FIELD

The present invention relates to droplet microfluidic devices, and more specifically to Active Matrix Electrowetting-On-Dielectric (AM-EWOD) devices and control methods for actuating device elements.

BACKGROUND ART

Electrowetting on dielectric (EWOD) is a well-known technique for manipulating droplets of fluid by the application of an electric field. Active Matrix EWOD (AM-EWOD) refers to implementation of EWOD in an active matrix array incorporating transistors, for example by using thin film transistors (TFTs). It is thus a candidate technology for digital microfluidics for lab-on-a-chip technology. An introduction to the basic principles of the technology can be found in "Digital microfluidics: is a true lab-on-a-chip possible?", R. B. Fair, Microfluid Nanofluid (2007) 3:245-281).

FIG. 1 shows a part of a conventional EWOD device in cross section. The device includes a lower substrate 10, the uppermost layer of which is formed from a conductive material which is patterned so that a plurality of array element electrodes 12 (e.g., 12A and 12B in FIG. 1) are realized. The electrode of a given array element may be termed the element electrode 12. A liquid droplet 14, including a polar material (which is commonly also aqueous and/or ionic), is constrained in a plane between the lower substrate 10 and a top substrate 16. A suitable gap between the two substrates may be realized by means of a spacer 18, and a non-polar surround fluid 20 (e.g. oil) may be used to occupy the volume not occupied by the liquid droplet 14. An insulator layer 22 disposed upon the lower substrate 10 separates the conductive element electrodes 12A, 12B from a first hydrophobic coating 24 upon which the liquid droplet 14 sits with a contact angle 26 represented by θ. The hydrophobic coating is formed from a hydrophobic material (commonly, but not necessarily, a fluoropolymer).

On the top substrate 16 is a second hydrophobic coating 28 with which the liquid droplet 14 may come into contact. Interposed between the top substrate 16 and the second hydrophobic coating 28 is a reference electrode 30.

The contact angle θ is defined as shown in FIG. 1, and is determined by the balancing of the surface tension components between the solid-to liquid ($\gamma_{SL}$), the liquid-to non-polar surrounding fluid ($\gamma_{LG}$) and the solid to non-polar surrounding fluid ($\gamma_{SG}$) interfaces, and in the case where no voltages are applied satisfies Young's law, the equation being given by:

$$\cos\theta = \frac{\gamma_{SG} - \gamma_{SL}}{\gamma_{LG}} \quad \text{(equation 1)}$$

In operation, voltages termed the EW drive voltages, (e.g. $V_T$, $V_0$ and $V_{00}$ in FIG. 1) may be externally applied to different electrodes (e.g. reference electrode 30, element electrodes 12, 12A and 12B, respectively). The resulting electrical forces that are set up effectively control the hydrophobicity of the hydrophobic coating 24. By arranging for different EW drive voltages (e.g. $V_0$ and $V_{00}$) to be applied to different element electrodes (e.g. 12A and 12B), the liquid droplet 14 may be moved in the lateral plane between the two substrates 10 and 16.

Example configurations and operation of EWOD devices are described in the following. U.S. Pat. No. 6,911,132 (Pamula et al., issued Jun. 28, 2005) discloses a two dimensional EWOD array to control the position and movement of droplets in two dimensions. U.S. Pat. No. 6,565,727 (Shenderov, issued May 20, 2003) further discloses methods for other droplet operations including the splitting and merging of droplets, and the mixing together of droplets of different materials. U.S. Pat. No. 7,163,612 (Sterling et al., issued Jan. 16, 2007) describes how TFT based thin film electronics may be used to control the addressing of voltage pulses to an EWOD array by using circuit arrangements very similar to those employed in AM display technologies.

The approach of U.S. Pat. No. 7,163,612 may be termed "Active Matrix Electrowetting on Dielectric" (AM-EWOD). There are several advantages in using TFT based thin film electronics to control an EWOD array, namely:

Electronic driver circuits can be integrated onto the lower substrate 10.

TFT-based thin film electronics are well suited to the AM-EWOD application. They are cheap to produce so that relatively large substrate areas can be produced at relatively low cost.

TFTs fabricated in standard processes can be designed to operate at much higher voltages than transistors fabricated in standard CMOS processes. This is significant since many EWOD technologies require electro-wetting voltages in excess of 20V to be applied.

To perform various droplet operations in an AM-EWOD device, it can be desirable to be able to sense a droplet property, such as droplet size or location on the array of elements. US application 2010/0194408 (Sturmer et al., published Aug. 5, 2010) describes a method, circuit and apparatus for detecting capacitance on a droplet actuator, inter alia, for determining the presence, partial presence or absence of a droplet at an electrode. U.S. Pat. No. 8,653,832 (Hadwen et al., issued Feb. 18, 2014) describes how an impedance (capacitance) sensing function can be incorporated into the array element circuit of each array element of an AM-EWOD device. The impedance sensor circuit may be used for determining the presence and size of liquid droplets present at each electrode in the array.

Upon adequate sensing, droplet operations may then be performed, such as for example holding a droplet position, moving a droplet across the device, splitting a droplet into multiple droplets, mixing different droplets, and others. These various operations may be performed by actuating a suitable pattern of elements on the AM-EWOD device. For example, U.S. Pat. No. 7,569,129 (Pamula et al., issued Aug. 4, 2009) describes the use of element actuation to hold a droplet isolated from other droplets. Sturmer referenced above describes the use of capacitance detection as real time feedback to determine whether a droplet operation has been successful. WO2008055256A3 (Kim et al., published May 8, 2008) describes the use of capacitance detection as real time feedback to control the volume of a droplet being dispensed or split from a reservoir. Other actuation methods for performing various droplet operations are known.

Problem to be Solved by the Invention

The inventors have found that the electric fields generated from excessive or prolonged actuation of the EWOD or AM-EWOD elements can be damaging to both the subject droplet and to components of the device itself. The protocols performed on EWOD platforms may use reagents which are delicate and may be adversely affected by actuation. Damage to reagents and other functional chemicals contained within a droplet can result in undesirable bubbles forming within the droplet (for example due to the release of gas dissolved in the droplet or the surrounding oil). In addition, excessive or prolonged actuation may reduce the lifetime of the EWOD device as the electric fields involved can have deleterious effects on components of the device. For example, the insulator layers and the hydrophobic coatings have been found in particular to be susceptible to damage from the electric fields that result from prolonged actuation of the EWOD elements.

The present invention solves this problem through enhanced control of the actuation patterns of the EWOD elements. In particular, the control system and related control methods of the present invention operate to minimize the time over which EWOD elements are actuated while still effectively performing requisite droplet operations. By minimizing actuation time of the EWOD elements, which minimizes exposure to the generated electric fields, the propensity to damage the subject droplets or device components is reduced.

SUMMARY OF INVENTION

The present invention pertains to enhanced control systems and methods for the actuation of array elements in an EWOD device, and AM-EWOD devices in particular. The control system implements a method of driving the array elements by which intermittent actuation of pertinent array elements is employed to maintain a droplet in a desired state. By employing intermittent actuation patterns, the control system minimizes actuation time of the EWOD elements, which in turn minimizes exposure to the generated electric fields and the resultant damage to the subject droplets or device components.

In exemplary embodiments, the control system operates to apply suitable actuation voltages to pertinent array elements at a predetermined time, rate, and duration in accordance with a specified or preset duty cycle, regardless of the actual real time properties of the droplet. In other exemplary embodiments, the EWOD or AM-EWOD device incorporates one or more sensors, such as for example sensor circuitry within each array element circuit, which provides information and feedback regarding a droplet state. In embodiments employing sensor circuitry or other sensors, the control system operates to apply suitable actuation voltages only when an intervention is necessary to maintain the droplet in a desired state (e.g., to maintain droplet position and stop a droplet drifting out of position, maintain a particular droplet shape or aspect ratio, maintain a particular droplet size, prevent droplet collision with a second object or droplet, or the like).

The present invention provides for an enhance microfluidic system including an electro-wetting on dielectric (EWOD) device and a control system, and a related control method. The EWOD device includes an element array configured to receive one or more fluid droplets, the element array comprising a plurality of individual array elements. The control system is configured to control actuation voltages applied to the element array to perform manipulation operations as to the fluid droplets. In exemplary embodiments, the control system is configured to apply a sequence of actuation voltages to a portion of the array elements associated with a droplet to maintain the droplet in a desired droplet state corresponding to a predetermined droplet property. The sequence of actuation voltages includes an actuation-on period in which the portion of the array elements associated with the droplet is actuated and an actuation-off period in which the portion of the array elements associated with the droplet is not actuated, and the actuation-off period is non-zero.

In exemplary embodiments, the control system may be configured to apply a sequence of actuation voltages comprising a predetermined duty cycle including a predetermined time, rate and duration of actuation voltages to the portion of the array elements associated with the droplet. In exemplary embodiments, the system further may include a sensor for sensing a droplet state. With sensor based control, the control system may be configured to: receive droplet state information from the sensor; determine whether a droplet is in a state that deviates from the desired droplet state in accordance with predetermined criteria based on the droplet state information; and apply actuation voltages to the portion of the array elements associated with the droplet when the control system determines that the droplet state satisfies the predetermined criteria to return the droplet to the desired droplet state.

These and further features of the present invention will be apparent with reference to the following description and attached drawings. In the description and drawings, particular embodiments of the invention have been disclosed in detail as being indicative of some of the ways in which the principles of the invention may be employed, but it is understood that the invention is not limited correspondingly in scope. Rather, the invention includes all changes, modifications and equivalents coming within the spirit and terms of the claims appended hereto. Features that are described and/or illustrated with respect to one embodiment may be used in the same way or in a similar way in one or more other embodiments and/or in combination with or instead of the features of the other embodiments.

Advantageous Effects of the Invention

The control system and related control methods of the present invention operate to provide intermittent actuation of the array elements to minimize the time over which EWOD or AM-EWOD elements are actuated while still effectively performing requisite droplet operations (e.g. move, merge, split, dispense and hold). By minimizing actuation time of the EWOD or AM-EWOD elements, which minimizes exposure to the generated electric fields, the propensity to damage the subject droplets or device components is reduced. Intermittent actuation thus advantageously limits the duty cycle or time period over which the array elements and associated droplets are actuated. This improves the device reliability and/or prevents damage to chemically or biologically fragile reagents within the droplet.

BRIEF DESCRIPTION OF DRAWINGS

FIG. 5A is a drawing depicting a circuit representation of the electrical load presented at the element electrode when a liquid droplet is present.

FIG. 5B is a drawing depicting a circuit representation of the electrical load presented at the element electrode when no liquid droplet is present.

FIG. 7 is a drawing depicting an exemplary arrangement of the array element circuit in accordance with embodiments of the present invention.

FIG. 8 is a drawing depicting a sequence of electrode actuation comprising a duty cycle for maintaining droplet position on an array of elements in an EWOD device.

FIG. 9 is a drawing depicting a sequence of electrode actuation comprising a duty cycle for maintaining droplet shape on an array of elements in an EWOD device.

FIG. 10 is a drawing depicting a sequence of electrode actuation comprising a duty cycle for maintaining droplet size on an array of elements in an EWOD device.

FIG. 11 is a drawing depicting a sequence of electrode actuation comprising a sensor-based intervention for maintaining droplet position on an array of elements in an EWOD device.

FIG. 12 is a drawing depicting a sequence of electrode actuation comprising a sensor-based intervention for maintaining droplet shape on an array of elements in an EWOD device.

FIG. 13 is a drawing depicting a sequence of electrode actuation comprising a sensor-based intervention for maintaining droplet size on an array of elements in an EWOD device.

FIG. 14 is a drawing depicting a sequence of electrode actuation comprising a sensor-based intervention for maintaining droplet position on an array of elements in an EWOD device relative to a second object in the EWOD device.

DESCRIPTION OF EMBODIMENTS

Figure 1:
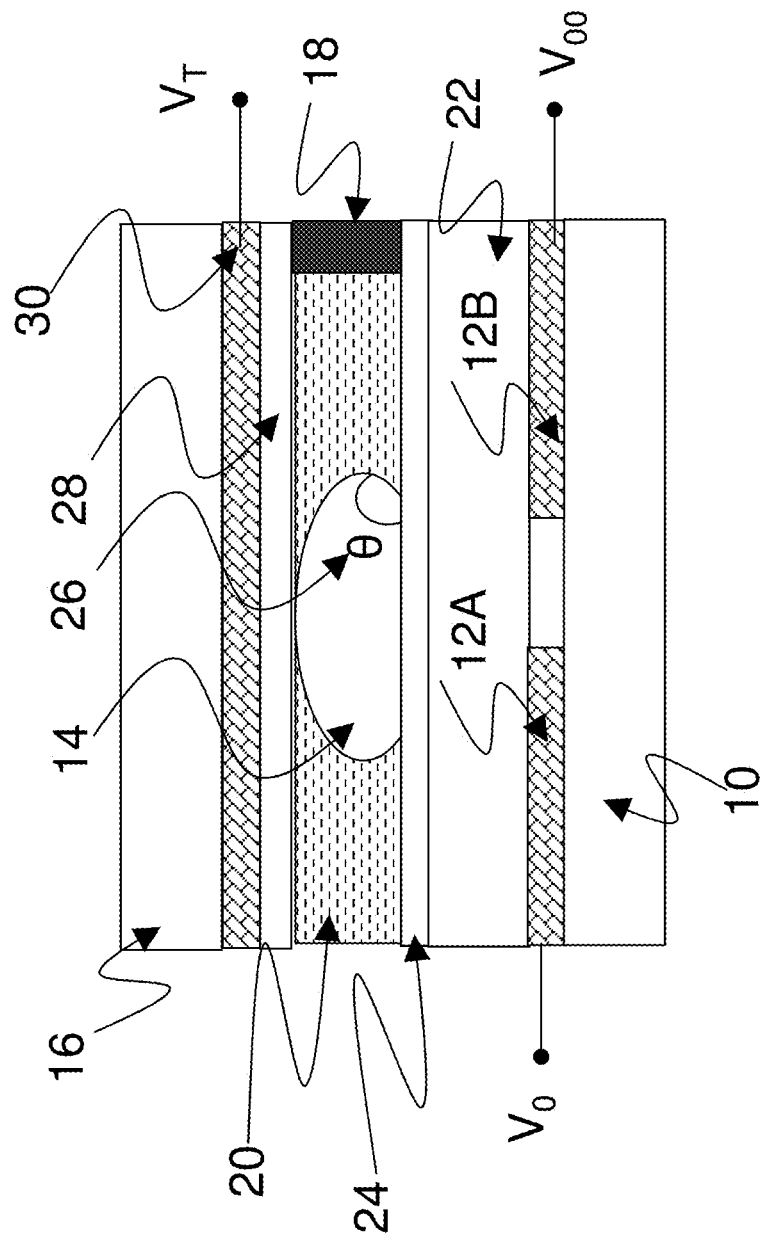
FIG. 1 is a drawing depicting a conventional EWOD device in cross-section.

Embodiments of the present invention will now be described with reference to the drawings, wherein like reference numerals are used to refer to like elements throughout. It will be understood that the figures are not necessarily to scale.

Figure 2:
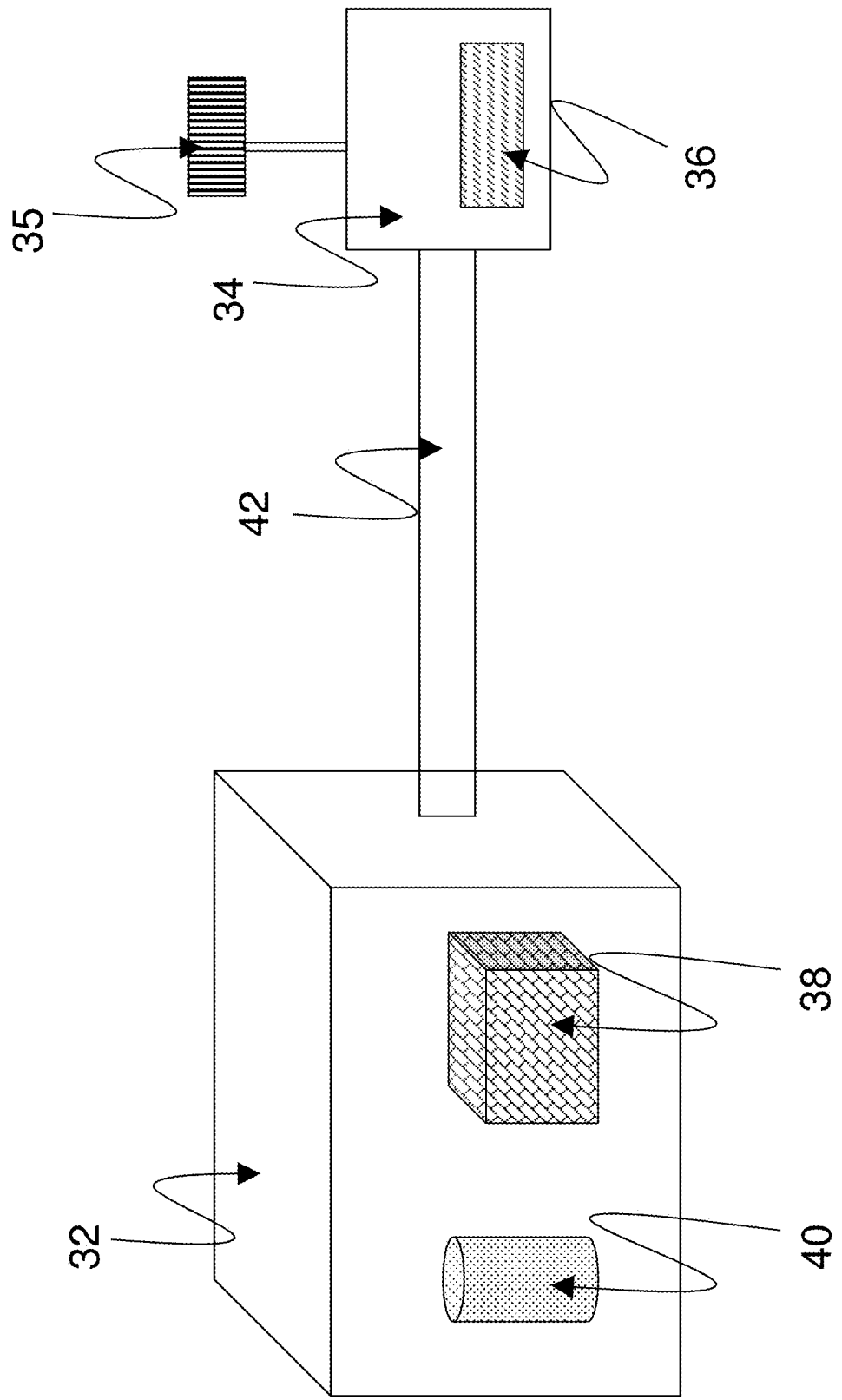
FIG. 2 is a drawing depicting an exemplary EWOD based microfluidic system according to embodiments of the present invention.

FIG. 2 is a drawing depicting an exemplary EWOD based microfluidic system according to embodiments of the present invention. In the example of FIG. 2, the measurement system includes a reader 32 and a cartridge 34. The cartridge 34 may contain a microfluidic device, such as an EWOD or AM-EWOD device 36, as well as (not shown) fluid input ports into the device and an electrical connection as are conventional. The fluid input ports may perform the function of inputting fluid into the AM-EWOD device 36 and generating droplets within the device, for example by dispensing from input reservoirs as controlled by electro-wetting.

As further detailed below, the microfluidic device includes an electrode array configured to receive the inputted fluid droplets.

The microfluidic system further may include a control system configured to control actuation voltages applied to the electrode array of the microfluidic device to perform manipulation operations to the fluid droplets. For example, the reader 32 may contain such a control system configured as control electronics 38 and a storage device 40 that may store any application software any data associated with the system. The control electronics 38 may include suitable circuitry and/or processing devices that are configured to carry out various control operations relating to control of the AM-EWOD device 36, such as a CPU, microcontroller or microprocessor.

Among their functions, to implement the features of the present invention, the control electronics may comprise a part of the overall control system that may execute program code embodied as a control application within the storage device 40. It will be apparent to a person having ordinary skill in the art of computer programming, and specifically in application programming for electronic control devices, how to program the control system to operate and carry out logical functions associated with the stored control application. Accordingly, details as to specific programming code have been left out for the sake of brevity. The storage device 40 may be configured as a non-transitory computer readable medium, such as random access memory (RAM), a read-only memory (ROM), an erasable programmable read-only memory (EPROM or Flash memory), or any other suitable medium. Also, while the code may be executed by control electronics 38 in accordance with an exemplary embodiment, such control system functionality could also be carried out via dedicated hardware, firmware, software, or combinations thereof, without departing from the scope of the invention.

The control system may be configured to perform some or all of the following functions:

- Define the appropriate timing signals to manipulate liquid droplets on the AM-EWOD device 36.
- Interpret input data representative of sensor information measured by a sensor or sensor circuitry associated with the AM-EWOD device 36, including computing the locations, sizes, centroids and perimeters of liquid droplets on the AM-EWOD device 36.
- Use calculated sensor data to define the appropriate timing signals to manipulate liquid droplets on the AM-EWOD device 36, i.e. acting in a feedback mode.
- Provide for implementation of a graphical user interface (GUI) whereby the user may program commands such as droplet operations (e.g. move a droplet), assay operations (e.g. perform an assay), and the GUI may report the results of such operations to the user.

In the example of FIG. 2, an external sensor module 35 is provided for sensing droplet properties. For example, optical sensors as are known in the art may be employed as external sensors for sensing droplet properties. Suitable optical sensors include camera devices, light sensors, charged coupled devices (CCDs) and image similar image sensors, and the like. As further detailed below, a sensor alternatively may be configured as internal sensor circuitry incorporated as part of the drive circuitry in each array element. Such sensor circuitry may sense droplet properties by the detection of an electrical property at the array element, such as impedance or capacitance.

The control system, such as via the control electronics 38, may supply and control the actuation voltages applied to the electrode array of the microfluidics device 36, such as required voltage and timing signals to perform droplet manipulation operations and sense liquid droplets on the AM-EWOD device 36. The control electronics further may execute the application software to generate and output control voltages for droplet sensing and performing sensing operations. The reader 32 and cartridge 34 may be electrically connected together while in use, for example by a cable of connecting wires 42, although various other methods (e.g. wireless connection) of providing electrical communication may be used as are known to those of ordinary skill in the art.

Figure 3:
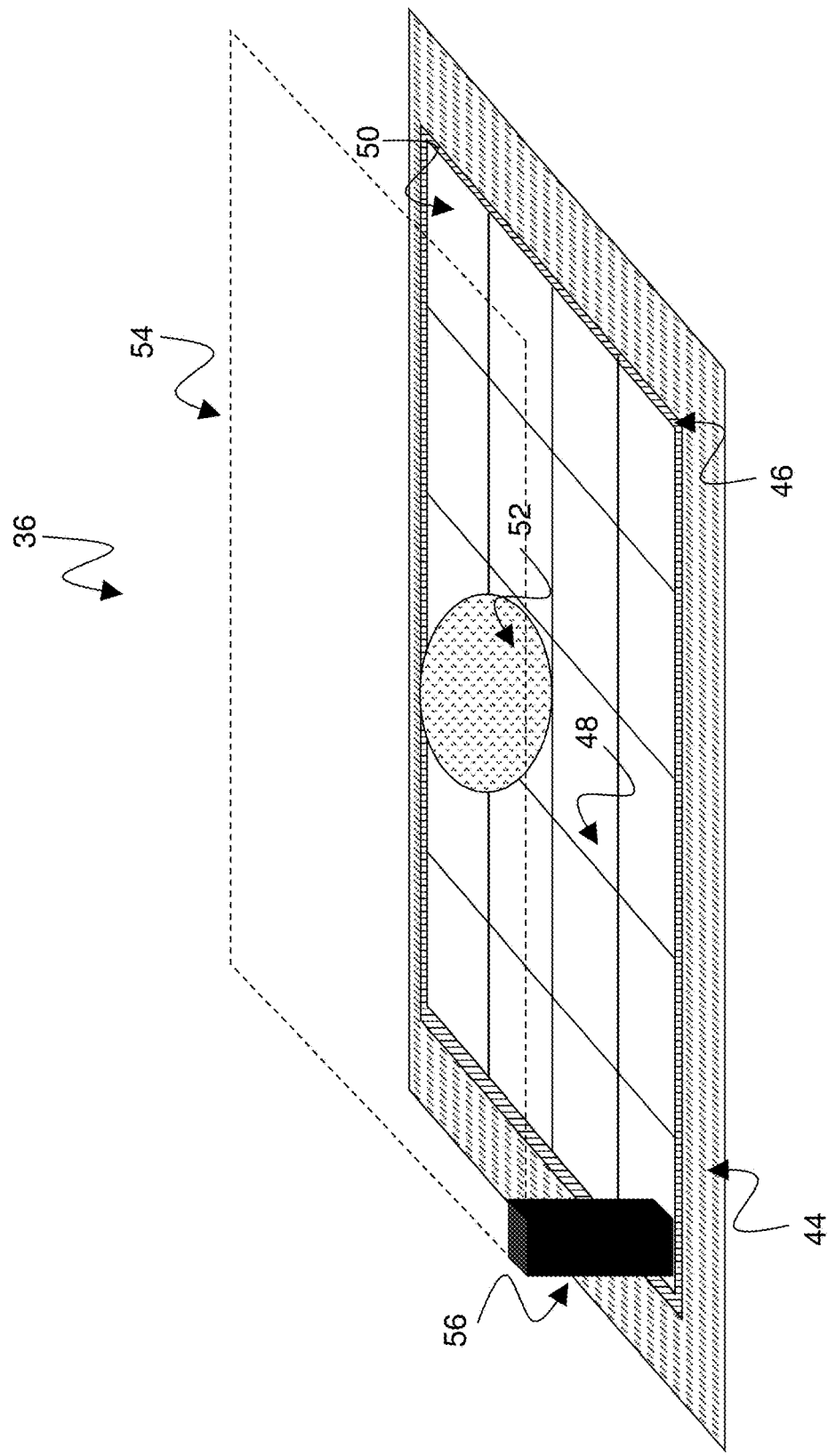
FIG. 3 is a drawing depicting an exemplary AM-EWOD device in schematic perspective in accordance with embodiments of the present invention.

FIG. 3 is a drawing depicting additional details of the exemplary AM-EWOD device 36 in schematic perspective in accordance with embodiments of the present invention. The AM-EWOD device 36 has a lower substrate 44 with thin film electronics 46 disposed upon the lower substrate 44. The thin film electronics 46 are arranged to drive array element electrodes 48. A plurality of array element electrodes 48 are arranged in an electrode or element array 50, having X by Y array elements where X and Y may be any integer. A liquid droplet 52 which may include any polar liquid and which typically may be aqueous, is enclosed between the lower substrate 44 and a top substrate 54 separated by a spacer 56, although it will be appreciated that multiple liquid droplets 52 can be present.

Figure 4:
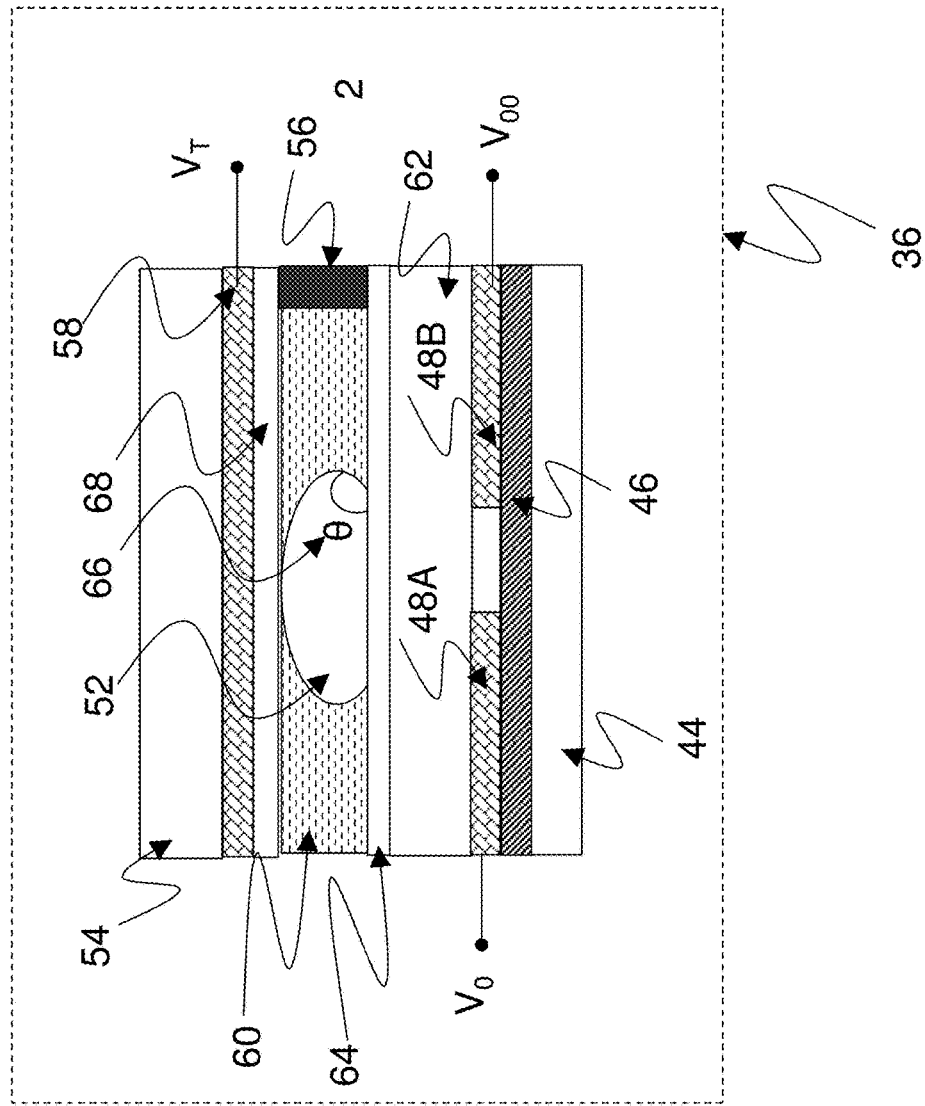
FIG. 4 is a drawing depicting a cross section through some of the array elements of the exemplary AM-EWOD device of FIG. 3.

FIG. 4 is a drawing depicting a cross section through some of the array elements of the exemplary AM-EWOD 36 device of FIG. 3. In the portion of the AM-EWOD device depicted in FIG. 4, the device includes a pair of the array element electrodes 48A and 48B that are shown in cross section that may be utilized in the electrode or element array 50 of the AM-EWOD device 36 of FIG. 3. The device configuration is similar to the conventional configuration shown in FIG. 1, with the AM-EWOD device 36 further incorporating the thin-film electronics 46 disposed on the lower substrate 44, which is separated from the upper substrate 54 by the spacer 56. The uppermost layer of the lower substrate 44 (which may be considered a part of the thin film electronics layer 46) is patterned so that a plurality of the array element electrodes 48 (e.g. specific examples of array element electrodes are 48A and 48B in FIG. 4) are realized. The term element electrode 48 may be taken in what follows to refer both to the physical electrode structure 48 associated with a particular array element, and also to the node of an electrical circuit directly connected to this physical structure. A reference electrode 58 is shown in FIG. 4 disposed upon the top substrate 54, but the reference electrode alternatively may be disposed upon the lower substrate 44 to realize an in-plane reference electrode geometry. The term reference electrode 58 may also be taken in what follows to refer to both or either of the physical electrode structure and also to the node of an electrical circuit directly connected to this physical structure.

Also similarly to the conventional structure of FIG. 1, in the AM-EWOD device 36, a non-polar fluid 60 (e.g. oil) may be used to occupy the volume not occupied by the liquid droplet 52. An insulator layer 62 may be disposed upon the lower substrate 44 that separates the conductive element electrodes 48A and 48B from a first hydrophobic coating 64 upon which the liquid droplet 52 sits with a contact angle 66 represented by θ. The hydrophobic coating is formed from a hydrophobic material (commonly, but not necessarily, a fluoropolymer). On the top substrate 54 is a second hydrophobic coating 68 with which the liquid droplet 52 may come into contact. The reference electrode 58 is interposed between the top substrate 54 and the second hydrophobic coating 68.

FIG. 5A shows a circuit representation of the electrical load 70A between the element electrode 48 and the reference electrode 58 in the case where a liquid droplet 52 is present. The liquid droplet 52 can usually be modeled as a resistor and capacitor in parallel. Typically, the resistance of the droplet will be relatively low (e.g. if the droplet contains ions) and the capacitance of the droplet will be relatively high (e.g. because the relative permittivity of polar liquids is relatively high, e.g. ~80 if the liquid droplet is aqueous). In many situations the droplet resistance is relatively small, such that at the frequencies of interest for electro-wetting, the liquid droplet 52 may function effectively as an electrical short circuit. The hydrophobic coatings 64 and 68 have electrical characteristics that may be modelled as capacitors, and the insulator 62 may also be modelled as a capacitor. The overall impedance between the element electrode 48 and the reference electrode 58 may be approximated by a capacitor whose value is typically dominated by the contribution of the insulator 62 and hydrophobic coatings 64 and 68 contributions, and which for typical layer thicknesses and materials may be on the order of a pico-Farad in value.

FIG. 5B shows a circuit representation of the electrical load 70B between the element electrode 48 and the reference electrode 58 in the case where no liquid droplet is present. In this case the liquid droplet components are replaced by a capacitor representing the capacitance of the non-polar fluid 60 which occupies the space between the top and lower substrates. In this case the overall impedance between the element electrode 48 and the reference electrode 58 may be approximated by a capacitor whose value is dominated by the capacitance of the non-polar fluid and which is typically small, of the order of femto-Farads.

For the purposes of driving and sensing the array elements, the electrical load 70A/70B overall functions in effect as a capacitor, whose value depends on whether a liquid droplet 52 is present or not at a given element electrode 48. In the case where a droplet is present, the capacitance is relatively high (typically of order pico-Farads), whereas if there is no liquid droplet present the capacitance is low (typically of order femto-Farads). If a droplet partially covers a given electrode 48 then the capacitance may approximately represent the extent of coverage of the element electrode 48 by the liquid droplet 52.

Figure 6:
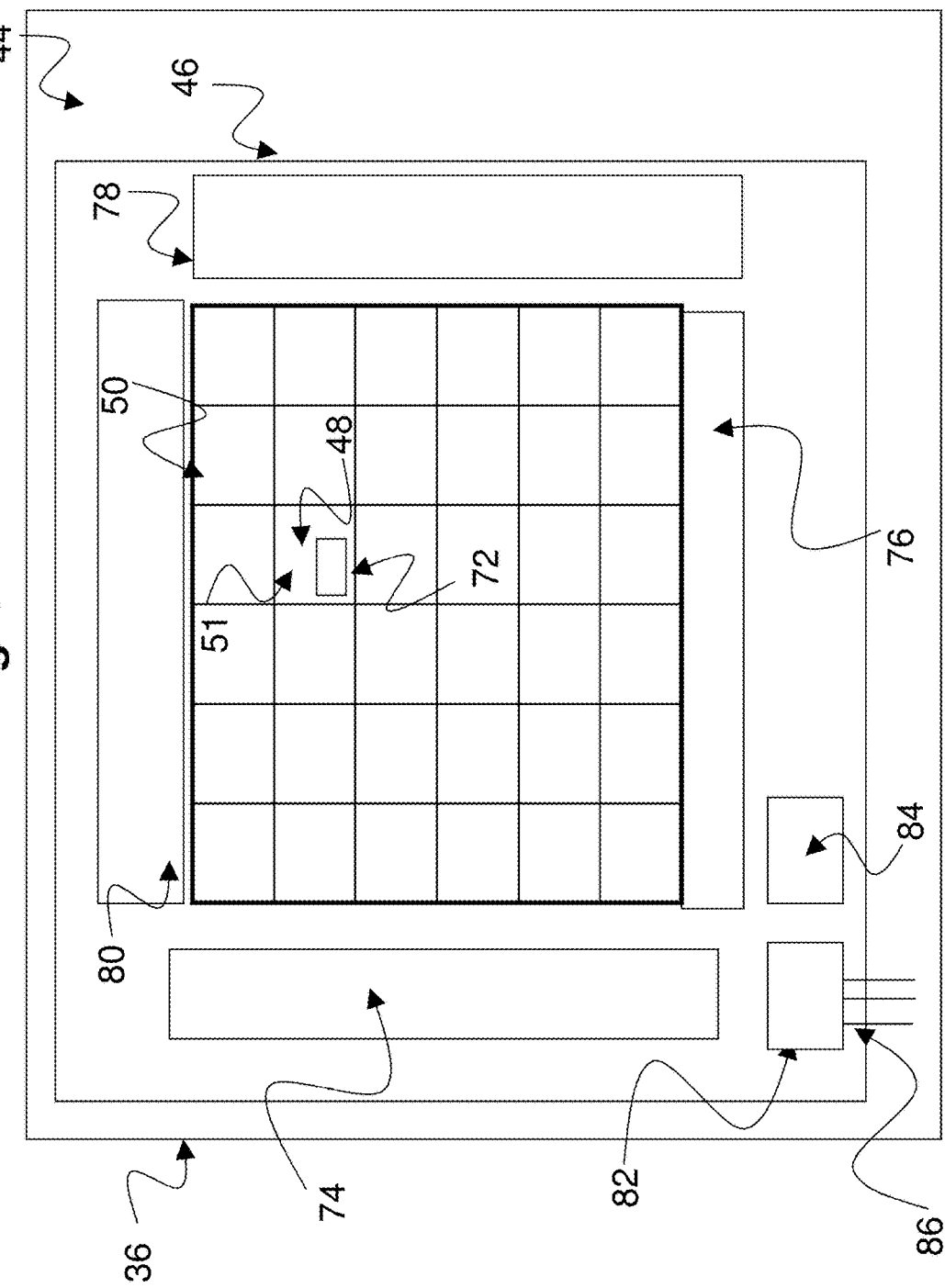
FIG. 6 is a drawing depicting an exemplary arrangement of thin film electronics in the exemplary AM-EWOD device of FIG. 3 in accordance with embodiments of the present invention.

FIG. 6 is a drawing depicting an exemplary arrangement of thin film electronics 46 in the exemplary AM-EWOD device 36 of FIG. 3 in accordance with embodiments of the present invention. The thin film electronics 46 is located upon the lower substrate 44. Each array element 51 of the array of elements 50 contains an array element circuit 72 for controlling the electrode potential of a corresponding element electrode 48. Integrated row driver 74 and column driver 76 circuits are also implemented in thin film electronics 46 to supply control signals to the array element circuit 72. The array element circuit 72 may also contain a sensing capability for detecting the presence or absence of a liquid droplet in the location of the array element. Integrated sensor row addressing 78 and column detection circuits 80 may further be implemented in thin film electronics for the addressing and readout of the sensor circuitry in each array element.

A serial interface 82 may also be provided to process a serial input data stream and facilitate the programming of the required voltages to the element electrodes 48 in the array 50. A voltage supply interface 84 provides the corresponding supply voltages, top substrate drive voltages, and other requisite voltage inputs as further described herein. A number of connecting wires 86 between the lower substrate 44 and external control electronics, power supplies and any other components can be made relatively few, even for large array sizes. Optionally, the serial data input may be partially parallelized. For example, if two data input lines are used the first may supply data for columns 1 to X/2, and the second for columns (1+X/2) to M with minor modifications to the column driver circuits 76. In this way the rate at which data can be programmed to the array is increased, which is a standard technique used in Liquid Crystal Display driving circuitry.

Generally, an exemplary AM-EWOD device 36 that includes thin film electronics 46 may be configured as follows. The AM-EWOD device 36 includes the reference electrode 58 mentioned above (which, optionally, could be an in-plane reference electrode) and a plurality of individual array elements 51 on the array of elements 50, each array element 51 including an array element electrode 48 and array element circuitry 72. Relatedly, the AM-EWOD device 36 may be configured to perform a method of actuating the array elements to manipulate liquid droplets on the array by controlling an electro-wetting voltage to be applied to a plurality of array elements. The applied voltages may be provided by operation of the control system described as to FIG. 2, including the control electronics 38 and applications and data stored on the storage device 40. The electro-wetting voltage at each array element 51 is defined by a potential difference between the array element electrode 48 and the reference electrode 58. The method of controlling the electro-wetting voltage at a given array element typically includes the steps of supplying a voltage to the array element electrode 48, and supplying a voltage to the reference electrode 58, by operation of the control system.

FIG. 7 is a drawing depicting an exemplary arrangement of the array element circuit 72 present in each array element 51, in accordance with embodiments of the present invention. The array element circuit 72 may contain an actuation circuit 88, having inputs ENABLE, DATA and ACTUATE, and an output which is connected to an element electrode 48. The array element circuit 72 also may contain a droplet sensor circuit 90, which may be in electrical communication with the element electrode 48. Typically, the read-out of the droplet sensor circuit 90 may be controlled by one or more addressing lines (e.g. RW) that may be common to elements in the same row of the array, and may also have one or more outputs, e.g. OUT, which may be common to all elements in the same column of the array.

The array element circuit 72 may typically perform the functions of:
(i) Selectively actuating the element electrode 48 by supplying a voltage to the array element electrode. Accordingly, any liquid droplet present at the array element 51 may be actuated or de-actuated by the electro-wetting effect.
(ii) Sensing the presence or absence of a liquid droplet at the location of the array element 51. The means of sensing may be capacitive, optical, thermal or some other means. Capacitive sensing may be employed conveniently and effectively using an impedance sensor circuit as part of the array element circuitry.

Exemplary configurations of array element circuits 72 including impedance sensor circuitry are known in the art, and for example are described in detail in U.S. Pat. No. 8,653,832 referenced in the background art section, and commonly assigned UK application GB1500261.1, both of which are incorporated here by reference. These patent documents include descriptions of how the droplet may be actuated (by means of electro-wetting) and how the droplet may be sensed by capacitive or impedance sensing means. Typically, capacitive and impedance sensing may be analogue and may be performed simultaneously, or near simultaneously, at every element in the array. By processing the returned information from such a sensor (for example in the application software in the storage device 40 of the reader 32), the control system described above can determine in real-time, or almost real-time the position, size, centroid and perimeter of each liquid droplet present in the array of elements 50. As referenced in connection with FIG. 2, an alternative to sensor circuitry is to provide an external sensor (e.g., sensor 35), such as an optical sensor that can be used to sense droplet properties.

The present invention pertains to an enhanced control system and control methods for the actuation of array elements in an EWOD device, including more specifically an AM-EWOD device. The control system implements a method of driving the array elements by which intermittent actuation of pertinent array elements is employed to maintain a droplet in a desired state. By employing an intermittent actuation, the control system minimizes actuation time of the AM-EWOD elements, which in turn minimizes exposure to the generated electric fields and the resultant damage to the subject droplets or device components.

Certain terms as used in the specification are defined as follows. The "state" of a droplet may refer to any property of the droplet such as size, shape, centroid position, aspect ratio, edge position, location on the device array, proximity to other objects on the device array, and the like. A "desired droplet state" may refer to a droplet state (i.e., any droplet property as above), that otherwise may be measured relative to a reference item, such as for example various components of the device such as the array elements, input or output ports and other physical structures in the device, other droplets in the device, and the like. A desired state typically may be thought of as a preferred droplet state as determined with reference to particular circumstances. A "sensor measurement" may refer to any means of measuring the droplet properties such as impedance measurements performed by an impedance sensor circuit in the array element circuitry, or optical measurements performed by an external optical sensor device (e.g., camera, light sensor, CCD and the like) as are known in the art. "Array elements associated with a droplet" are a subset of the array elements on an EWOD device that when actuated can control or affect a droplet state or otherwise manipulate a droplet.

Intermittent actuation is intended to provide actuation of array elements associated with a droplet for a sufficient amount of time to maintain the state of a droplet in a desired droplet state, while minimizing actuation time to substantially reduce the propensity to damage droplet constituents or device components.

Damage to the device may occur due to the exposure of the insulator 62 and hydrophobic coatings (64 and 68) to a high electric field, a situation that occurs when a droplet is actuated. In particular, the hydrophobic coatings are commonly formed from an electret material and thus have a tendency to trap charge, within them or at their interfaces. Trapped charge may have the effect of screening the applied electric field and reducing the actuation force applied to the droplet. Additionally, the high electric field may result in polarization of the insulator/hydrophobic coatings, which may also reduce the actuation strength. Additionally, the high electric field may occasionally result in defect paths forming through the insulator/hydrophobic coatings resulting in current flow, electrolysis and failure of the device.

Damage to the liquid due to exposure to the electric field may occur if the liquid contains components that may be denatured by the electric field, e.g. proteins, enzymes, cells or nucleic acids. The extent of the damage may be a function of the accumulated exposure time to the electric field.

When actuation voltages are turned off, small non-uniformities that may be present in droplet shape and thickness can result in migration or movement of the droplet. The result can be deviations of the droplet state away from a desired droplet state. For example, droplet size, shape, centroid position, edge position, location on the device array, and the like may change overtime in an undesirable manner that can undermine the purpose and use of the droplet, and perhaps undesirably result in the droplet coming in contact with or otherwise interfering with other droplets in close proximity. When such deviations occur, intermittent actuation can be performed to return the droplet from a current droplet state to a desired droplet state. The following are non-limiting example reasons why a droplet may deviate over time:

1. The spacing between the top substrate 54 and bottom substrate 44 (e.g. as controlled by the spacer 56) may be non-uniform over the lateral extent of the droplet. A non-uniform spacing may result in a difference in the Laplace pressure (the internal droplet pressure, determined in part by the constraining dimensions) over the lateral extent of the droplet. This will result in a lateral force, causing the droplet to move towards the part of the device where the spacing between the substrates is greater.
2. If either of the hydrophobic coatings 64 and 68 may be slightly non-uniform so as to have a differing hydrophobicity over the lateral extent of the droplet, the droplet may move or change shape of its own accord to cover the area of lower hydrophobicity.
3. If the profile of the droplet in plan-view is non-circular, the droplet may be observed to relax over time into a more circular shape.
4. If the whole device is operated on a non-horizontal surface, the droplet may drift over time due to the effects of gravity.

In general, in accordance with principles of the present invention, a sequence of actuation of array elements associated with a droplet in an EWOD device is performed wherein a ratio of the actuation-on period to actuation-off period is less than infinite, i.e., the actuation-off period is non-zero meaning that the actuation voltages are not applied for at least a portion of the sequence of actuation. In this regard, the inventors have observed that droplet changes in state tend to occur very gradually over time (and sometimes not at all if the device and/or droplet is highly uniform). Accordingly, an actuation-off time period in which actuation voltages are not applied can be significantly greater than an actuation-on period in which the actuation voltages are applied to the array elements associated with a droplet. The figures described below illustrate different sequences of actuation of array elements associated with a droplet in accordance with various control methods in accordance with the principles of the present invention.

The present invention provides for an enhance microfluidic system including an electro-wetting on dielectric (EWOD) device and a control system, and a related control method. The EWOD device includes an element array configured to receive one or more fluid droplets, the element array comprising a plurality of individual array elements. The control system is configured to control actuation voltages applied to the element array to perform manipulation operations as to the fluid droplets. In exemplary embodiments, the control system is configured to apply a sequence of actuation voltages to a portion of the array elements associated with a droplet to maintain the droplet in a desired droplet state corresponding to a predetermined droplet property. The sequence of actuation voltages includes an actuation-on period in which the portion of the array elements associated with the droplet is actuated and an actuation-off period in which the portion of the array elements associated with the droplet is not actuated, and the actuation-off period is non-zero. In exemplary embodiments, the control system may be configured to apply a sequence of actuation voltages comprising a predetermined duty cycle, and/or the actuation voltages may be applied in accordance with a sensor based intervention.

FIGS. 8-15 are drawings depicting sequences of electrode actuation of array elements associated with a droplet in an EWOD device, the sequences being performed for maintaining or establishing a desired state of a droplet in the EWOD device. Generally, such figures depict an array of elements 100 that is comparable to the array of elements 50 described above. The additional details of the EWOD device are omitted from these figures for convenience of illustration, but an EWOD device employing the array of elements 100 may be configured as described above with respect to FIGS. 2-7. Accordingly, the array of elements 100 may include individual array elements 102 each comparable to the array element 51, and each for example thus including electrodes 48 and 58, and the corresponding array element circuitry 72 which may include a droplet sensor circuit 90, such as for example an impedance or capacitive sensing circuit. As defined above, array elements associated with a droplet refers to a portion of the array elements on an EWOD device that when actuated can control of affect a droplet state or otherwise manipulate a droplet. In the examples of FIGS. 8-15, array elements 102a are designated as being associated with a droplet 104, and remaining array elements 102b are in regions of the array in which the array elements are not associated with the droplet 104, i.e., the array elements 102b are not involved in controlling or affecting the droplet state.

In exemplary embodiments, the control system operates to apply suitable actuation voltages to perform a sequence of electrode actuation of array elements associated with a droplet at a predetermined time, rate, and duration in accordance with a specified or preset duty cycle, regardless of the actual real time properties constituting the state of the droplet. In general, a predetermined duty cycle may be configured whereby a ratio of the actuation-on period to actuation-off period is less than infinite, i.e., again, the actuation-off period is non-zero meaning that the actuation voltages are not applied for at least a portion of the duty cycle. As referenced above, droplet changes in state may occur very gradually over time which permits the actuation-off period to be significantly greater than the actuation-on period. Based on such observation, a suitable duty cycle may be characterized by approximately 10% actuation-on/90% actuation-off, i.e., a ratio of actuation-on period to actuation-off period is less than or equal to 1:10. Under such parameters, an example of a suitable duty cycle may be to apply actuation voltages to electrodes of array elements associated with a droplet for 0.5 seconds once every 5.0 seconds. Other suitable duty cycles may be employed as may be appropriate to particular circumstances or applications.

In other circumstances, droplet changes in state may occur more rapidly over time, which requires that the actuation-off period not be as significantly greater than the actuation-on period. For example, during loading of the droplet into the EWOD device, its size changes relatively rapidly and in order to maintain a desirable droplet state (such as, but not limited to, a desirable droplet centroid position or droplet aspect ratio) a suitable duty cycle may be characterized by a ratio of actuation-on period to actuation-off period greater than or equal to 1:2. Under such parameters, an example of a suitable duty cycle may be to apply actuation voltages to electrodes of array elements associated with a droplet of 0.5 seconds every 1.5 seconds. Again, any suitable duty cycles may be employed as may be appropriate to particular circumstances or applications.

FIGS. 8-10 are drawings depicting sequences of electrode actuation comprising a predetermined duty cycle for maintaining a desired state of a droplet on an associated array of elements in an EWOD device. In the example of FIG. 8, a sequence of electrode actuation comprising a predetermined duty cycle is applied for maintaining droplet position on the array of elements 100. The steps of the sequence of actuation in FIG. 8 respectively are labeled A, B, C, and D. Further in the example of FIG. 8, there are nine array elements 102a associated with the droplet 104, which can be actuated to maintain a current position of the droplet 104 on the array 100. It will be appreciated that the number and position of elements associated with the droplet can be varied as suitable for any particular circumstances. The remaining elements 102b are in regions of the array that are not associated with the droplet 104, i.e., the droplets 102b are not involved in maintaining the droplet current position and thus remain unactuated during the entire actuation sequence A-D.

The sequence of actuation of FIG. 8 illustrates a duty cycle of alternating actuation-off periods, sequence steps A and C, with actuation-on periods, sequence steps B and D. As shown in FIG. 8, during the actuation-off periods, the droplet 104 is located at a particular position on the array 100. To ensure that the droplet 104 maintains this position, periodically the control system applies actuation voltages to the portion of array elements 102a associated with the droplet. When actuated, the electrical field draws the droplet to the array element electrodes. As shown in sequence steps B and D, the boundary of droplet 104 is drawn by the electric field to be commensurate with the actuated array element boundaries. When the actuation voltages are removed, the droplet 104 resumes its unactuated state as shown, for example, from the progression of sequence step B to step C.

By applying intermittent actuation in accordance with the predetermined duty cycle, the droplet 104 generally maintains its desired state and does not move substantially from the initial position of sequence step A. Again, because droplet changes in state occur very gradually over time, the actuation-off period may be significantly greater than the actuation-on period (e.g., ratio actuation-on period to actuation-off period is no greater than 1:10).

FIG. 9 is a variation in which a sequence of electrode actuation comprises a predetermined duty cycle for maintaining a desired shape or aspect ratio of a droplet. The steps of the sequence of actuation in FIG. 9 similarly are respectively labeled A, B, C, and D. Further in the example of FIG. 9, there are 32 array elements 102a associated with the droplet 104 due to the elongated or ovular shape of the droplet 104 in the desired state shown in sequence step A. The array elements 102a can be actuated to maintain such shape and aspect ratio of the droplet 104 on the array 100. The sequence of actuation of FIG. 9, therefore, illustrates a duty cycle of alternating actuation-off periods, sequence steps A and C, with actuation-on periods, sequence steps B and D. During the actuation-off periods, the droplet 104 maintains the desired ovular and elongated shape on the array 100. To ensure that the droplet 104 maintains this shape, periodically the control system applies actuation voltages to the portion of array elements 102a associated with the droplet. When actuated, the electrical field draws the droplet to the array element electrodes. As shown in sequence steps B and D, the boundary of droplet 104 is drawn by the electric field to be commensurate with the actuated array element boundaries. When the actuation voltages are removed, the droplet 104 resumes its unactuated state as shown, for example, from the progression of sequence step B to step C. A comparable duty cycle may be employed in the sequence of FIG. 9 as in FIG. 8.

FIG. 10 is a variation in which a sequence of electrode actuation comprises a predetermined duty cycle for maintaining a desired size of a droplet. The steps of the sequence of actuation in FIG. 10 similarly are respectively labeled A-F. Further in the example of FIG. 10, there are nine array elements 102a associated with the droplet 104 that may be actuated to maintain the desired size of the droplet 104 shown in sequence step A. The array elements 102a can be actuated to maintain such size of the droplet 104 on the array 100. The sequence of actuation of FIG. 10, therefore, illustrates a duty cycle of alternating actuation-off periods, sequence steps A-B and D-E, with actuation-on periods, sequence steps C and F. A comparable duty cycle may be employed in the sequence of FIG. 10 as in FIGS. 8-9.

The example of FIG. 10 illustrates the potential for migration of droplet material to change the state of the droplet from the desired state during the actuation-off period. In this particular example of droplet size, during the actuation-off period spanning steps A-B, the droplet has spread out and the size has changed in the sense that the droplet covers more of the array 100 in step B than in the desired state of step A. When actuated, the electrical field draws the droplet to the actuated array element electrodes. As shown in sequence step C, the boundary of droplet 104 is drawn by the electric field to be commensurate with the actuated array element boundaries. When the actuation voltage is removed, the droplet 104 resumes its unactuated state as shown, for example, from the progression of sequence steps C to D. In this example, there actually is no droplet migration during the actuation-off period spanning sequence steps D-E. However, because actuation occurs in accordance with a predetermined or preset duty cycle, the electrodes 102a are actuated at sequence step F even though the droplet state has not changed, insofar as the predetermined duty cycle is independent of the real-time state of the droplet. Migration can also change the state of the droplet from the desired state with respect to location (FIG. 8) or shape (FIG. 9), or other droplet properties, with actuation in accordance with the duty cycle then returning the droplet to the state corresponding to the desired state of the droplet.

In exemplary embodiments, the control system may store and execute any number of predetermined or preset duty cycles as executable program code as part of the control application. For example, the control application may include executable program code for any number of duty cycles for different operational modes of the device, which may be stored in the storage device 40 and executed by processor devices of the control electronics 38 (see FIG. 2). Initiation of a particular duty cycle may be initiated by user selection through interface devices of the control electronics, or otherwise selected automatically as part of the control application. In addition, the control application may be executed to apply different duty cycles to different portions of the array of elements.

In other exemplary embodiments, the AM-EWOD device incorporates one or more sensors, such as for example sensor circuitry 90 within each array element, or external sensors 35, that provide information and feedback regarding a droplet state. In embodiments employing sensor circuitry or other sensors, the control system operates to apply suitable actuation voltages only when an intervention is necessary to maintain the droplet in a desired state based on data gathered by the sensors (e.g., to maintain droplet position and stop a droplet drifting out of position, maintain a particular droplet shape, maintain a particular droplet size, or the like). For example, the control system may determine when a droplet state has deviated from a desired state by a predetermined amount or other predetermined criteria, and apply actuation voltages to array elements associated with the droplet to return the droplet to the desired state.

In exemplary embodiments of the invention, therefore, the microfluidic system further may include a sensor for sensing a droplet state. The control system may be configured to: receive droplet state information from the sensor; determine whether a droplet is in a state that deviates from the desired droplet state in accordance with predetermined criteria based on the droplet state information; and apply actuation voltages to the portion of the array elements associated with the droplet when the control system determines that the droplet state satisfies the predetermined criteria to return the droplet to the desired droplet state.

FIGS. 11-15 are drawings depicting a sequence of electrode actuation comprising a sensor-based intervention for maintaining a desired state of a droplet on an associated array of elements in an EWOD device. In the example of FIG. 11, a sequence of electrode actuation comprising a sensor-based intervention is applied for maintaining droplet position on the array of elements 100. The steps of the sequence of actuation in FIG. 11 respectively are labeled A-E. Further in the example of FIG. 11, there are nine array elements 102a associated with the droplet 104, which can be actuated to maintain a current position of the droplet 104 on the array 100. Again, the number and position of elements associated with the droplet can be varied as suitable for any particular circumstances. The remaining droplets 102b are in regions of the array that are not associated with the droplet 104, i.e., the droplets 102b are not involved in maintaining the droplet current position and thus remain unactuated during the entire actuation sequence A-F.

As shown in FIG. 11, sequence step A is an actuation-off period in which the droplet 104 is located at a particular position on the array 100. In sequence step B, the droplet has drifted from the desired state position of sequence step A. The droplet position may be tracked by the sensor until the droplet has deviated from the desired position by a predetermined amount or other predetermined criteria. In the example of FIG. 11, the droplet position drifts further until at sequence step C, the droplet 104 has deviated from the desired position by a predetermined amount. Accordingly, at sequence step C the control system applies actuation voltages to the portion of array elements 102a associated with the droplet. When actuated, the electrical field draws the droplet to the array element electrodes, and as shown in sequence step D, the droplet 104 is drawn by the electric field to be commensurate with the actuated array element boundaries. The result is the droplet 104 is drawn back to the position of the desired state, and when the actuation voltages are removed as shown in sequence step E, the droplet 104 resumes its unactuated state located back at the desired position commensurate with sequence step A.

By applying intermittent actuation in accordance with the sensor information, the droplet 104 generally maintains its desired state and any deviations from the initial position of sequence step A beyond predetermined criteria are eliminated. Again, because droplet changes in state occur very gradually over time, the actuation-off period may be significantly greater than the actuation-on period. In addition, by using sensor-based actuation, the actuation-off period is minimized insofar as actuation voltages are applied only as needed to return the droplet to the desired state (the desired position in the example of FIG. 11). Comparable actuation control may be applied to properties associated with any suitable desired state, as described with respect to the examples of the additional figures below.

FIG. 12 is a variation in which a sequence of electrode actuation comprises a sensor-based intervention for maintaining a desired shape or aspect ratio of a droplet. The steps of the sequence of actuation in FIG. 12 similarly are respectively labeled A-E. Sequence step A is an actuation-off period in which the droplet 104 has a particular shape and aspect ratio on the array 100. Further in the example of FIG. 12, there are 32 array elements 102a associated with the droplet 104 due to the elongated or ovular shape of the droplet 104 in the desired state shown in sequence step A. In sequence step B, the droplet has deviated from the desired state shape of sequence step A, flattening out to become more circular. The droplet shape and aspect ratio may be tracked by the sensor until the droplet has deviated from the desired shape of sequence step A by a predetermined amount or other predetermined criteria. Accordingly, at sequence step C the control system applies actuation voltages to the portion of array elements 102a associated with the droplet. When actuated, the electrical field draws the droplet to the array element electrodes, and as shown in sequence step D, the droplet 104 is drawn by the electric field to be commensurate with the actuated array element boundaries. The result is the droplet 104 is drawn back to the shape and aspect ratio of the desired state, and when the actuation voltages are removed as shown in sequence step E, the droplet 104 resumes its unactuated state having the desired shape and aspect ratio commensurate with sequence step A.

FIG. 13 shows a variation in which a sequence of electrode actuation comprises a sensor-based intervention for maintaining a desired size of a droplet. The steps of the sequence of actuation in FIG. 13 similarly are respectively labeled A-E. Sequence step A is an actuation-off period in which the droplet 104 has a particular size on the array 100. In sequence step B, the droplet has deviated from the desired state size of sequence step A, widening out into a larger circle. The droplet size may be tracked by the sensor until the droplet has deviated from the desired size by a predetermined amount or other predetermined criteria. In the example of FIG. 13, the droplet size deviates further until at sequence step C, the droplet 104 has deviated from the desired size by a predetermined amount. Accordingly, at sequence step C the control system applies actuation voltages to the portion of array elements 102a associated with the droplet. When actuated, the electric field draws the droplet to the array element electrodes, and as shown in sequence step D, the droplet 104 is drawn by the electric field to be commensurate with the actuated array element boundaries. The result is the droplet 104 is drawn back to the size of the desired state, and when the actuation voltages are removed as shown in sequence step E, the droplet 104 resumes its unactuated state with the desired size commensurate with sequence step A.

FIG. 14 shows another variation in which a sequence of electrode actuation comprises a sensor-based intervention for maintaining a desired position of a droplet, similar to FIG. 11. The steps of the sequence of actuation in FIG. 14 similarly are respectively labeled A-E. In this particular example, the droplet 104 also is positioned in proximity to a second object whose position is known and with which a collision is non-desirable. In the specific example of FIG. 14, the second object is a second droplet 106, whose position also may be sensed by any suitable sensor (e.g., impedance sensor circuit or suitable external sensor). The second object, however, may be an object other than another droplet, such as for example a physical barrier within the device, like a device wall or spacer.

As shown in the example of FIG. 14, sequence step A is an actuation-off period in which the first droplet 104 is located at a particular position on the array 100 with suitable spacing apart from the second object (e.g., second droplet) 106. In sequence step B, the first droplet 104 has drifted from the desired state position of sequence step A. The droplet position may be tracked by the sensor until the first droplet 104 has deviated from the desired position by a predetermined amount or other predetermined criteria. In this example, the predetermined criteria may be a threshold proximity to the second object (e.g., second droplet 106), which can present a potential for collision. In the example of FIG. 14, the first droplet position drifts further until at sequence step C, the first droplet 104 has deviated from the desired position in accordance with the predetermined criteria being in close proximity to the second droplet 106. Accordingly, at sequence step C the control system applies actuation voltages to the portion of array elements 102a associated with the first droplet 104. When actuated, the electrical field draws the first droplet to the array element electrodes, and as shown in sequence step D, the first droplet 104 is drawn by the electric field to be commensurate with the actuated array element boundaries. The result is the first droplet 104 is drawn back to the position of the desired state, and when the actuation voltages are removed as shown in sequence step E, the first droplet 104 resumes its unactuated state located back at the desired position suitably spaced apart from the second droplet 106 commensurate with sequence step A.

Figure 15A:
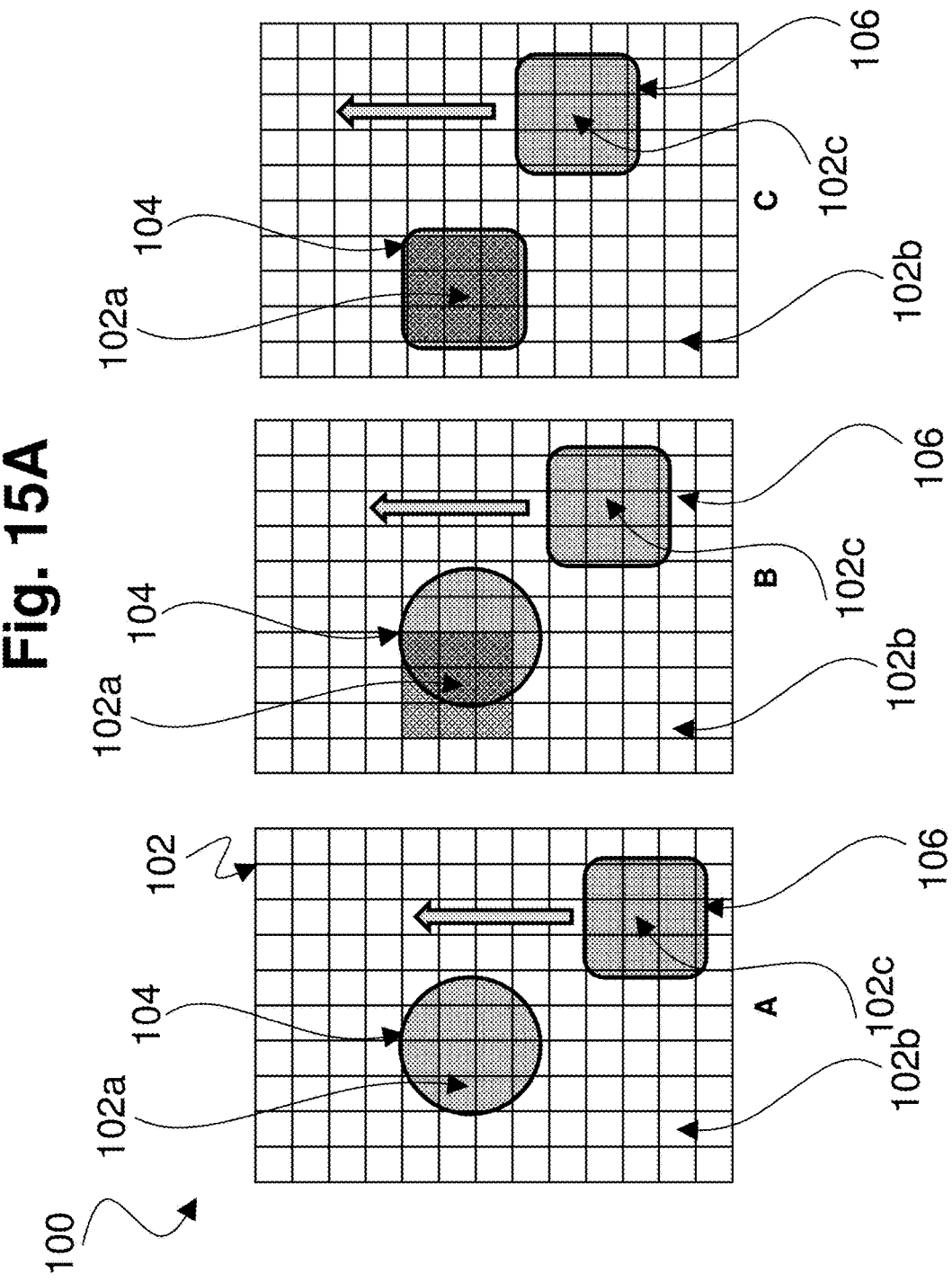
FIG. 15A and FIG. 15B are drawings depicting a sequence of electrode actuation comprising a sensor-based intervention for maintaining droplet position of a first droplet relative to a second moving droplet on an array of elements in an EWOD device.
Figure 15B:
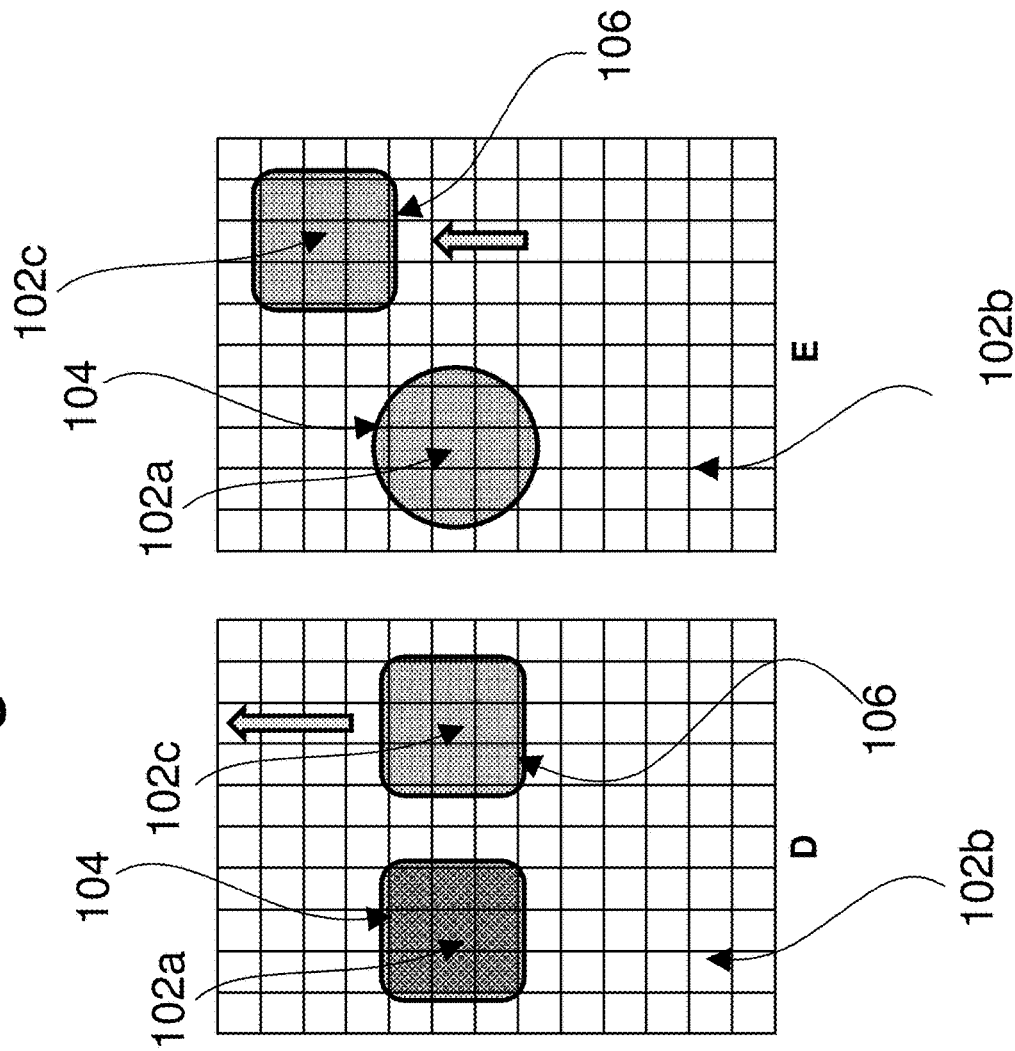

FIGS. 15A and 15B show another variation in which a sequence of electrode actuation comprises a sensor-based intervention for maintaining a desired position of a droplet, similar to FIG. 14 except the second droplet 106 is being moved across the array 100 in a direction indicated by the arrows in the sub-figures. As referenced above, the position of the second droplet 106 also may be sensed by any suitable sensor (e.g., impedance sensor circuit or suitable external sensor), and the movement of the second droplet 106 may be achieved by a sequential actuation of another portion of the array elements 102c associated with moving the second droplet 106 as is known in the art. A collision of the two droplets is undesirable, and the steps of the sequence of actuation in FIGS. 15A and 15B to avoid such a collision is shown similarly in sequence steps A-E.

As shown in the example of FIGS. 15A and 15B, sequence step A is an actuation-off period in which the first droplet 104 is located at a particular position on the array 100 without suitable spacing apart from a path of the moving second droplet 106 indicated by the arrow. At such position, there is a potential for collision with the moving second droplet 106. As in previous embodiments, the droplet position may be tracked by the sensor to determine if the droplet position is different from a desired position by a predetermined amount or other predetermined criteria. In this example, the predetermined criteria may be a threshold proximity to the path of the moving second droplet 106, which can present a potential for collision. In this example, in view of the path of the moving second droplet 106, the droplet state of sequence step A can be considered a non-desirable state even though such position previously may have been a desirable state. Accordingly, at sequence step B the control system applies actuation voltages to the portion of array elements 102a associated with the first droplet 104. When actuated, the electrical field draws the first droplet to the array element electrodes, and as shown in sequence step C, the first droplet 104 is drawn by the electric field to be commensurate with the actuated array element boundaries. The result is the first droplet 104 is drawn to the position of a desired state suitably spaced apart from the path of the moving droplet 106. This actuation may be maintained as shown in sequence step D as the second droplet 106 passes the first droplet 104, thereby precluding any collision. When the actuation voltages are removed as shown in sequence step E, the first droplet 104 resumes its unactuated state located now at the desired position suitably spaced apart from the second droplet 106. Alternatively, after the second droplet 106 has passed the first droplet 104, the control system may apply actuation voltages to a portion of array elements as appropriate to return the droplet to the initial position of sequence step A.

The control system and related control methods of the present invention, therefore, operate to provide intermittent actuation of the array elements to minimize the time over which EWOD or AM-EWOD elements are actuated while still effectively performing requisite droplet operations. By minimizing actuation time of the array elements, which minimizes exposure to the generated electric fields, the propensity to damage the subject droplets or device components is reduced. Intermittent actuation thus advantageously limits the time period over which the array elements and associated droplet are actuated. This improves the device reliability and/or prevents damage to chemically or biologically fragile reagents within the droplet.

Because the sensor-based intervention is targeted to the droplet state, more optimized actuation time periods are achieved, and therefore sensor-based intervention is preferred in EWOD systems that employ sensors. The presence of sensors, however, is not beneficial or feasible in all EWOD applications or technologies. For example, sensors typically are not employed in passive EWOD devices, and in some EWOD devices the pixel size may be too small to incorporate effective sensor circuitry or other sensors. For such EWOD devices that do not employ sensors, intermittent actuation by a preset or predetermined duty cycle is advantageous.

As aspect of the invention, therefore, is an enhanced microfluidic system including an electro-wetting on dielectric (EWOD) device comprising an element array configured to receive one or more fluid droplets, the element array comprising a plurality of individual array elements, and a control system configured to control actuation voltages applied to the element array to perform manipulation operations as to the fluid droplets. In exemplary embodiments, the control system is configured to apply a sequence of actuation voltages to a portion of the array elements associated with a droplet to maintain the droplet in a desired droplet state corresponding to a predetermined droplet property. The sequence of actuation voltages includes an actuation-on period in which the portion of the array elements associated with the droplet is actuated and an actuation-off period in which the portion of the array elements associated with the droplet is not actuated, and the actuation-off period is non-zero. The microfluidic system may include one or more of the following features, either individually or in combination.

In an exemplary embodiment of the microfluidic system, the control system is configured to apply a sequence of actuation voltages comprising a predetermined duty cycle including a predetermined time, rate and duration of actuation voltages to the portion of the array elements associated with the droplet.

In an exemplary embodiment of the microfluidic system, the actuation-off period of the duty cycle is greater than the actuation-on period of the duty cycle.

In an exemplary embodiment of the microfluidic system, a ratio of the actuation-on period of the duty cycle to the actuation-off period of the duty cycle is less than or equal to 1:10.

In an exemplary embodiment of the microfluidic system, the system further includes a sensor for sensing a droplet state, and the control system is configured to: receive droplet state information from the sensor; determine whether a droplet is in a state that deviates from the desired droplet state in accordance with predetermined criteria based on the droplet state information; and apply actuation voltages to the portion of the array elements associated with the droplet when the control system determines that the droplet state satisfies the predetermined criteria to return the droplet to the desired droplet state.

In an exemplary embodiment of the microfluidic system, the sensor comprises sensor circuitry incorporated into one or more array elements.

In an exemplary embodiment of the microfluidic system, the predetermined droplet property of the desired droplet state is based on at least one of droplet position on the element array, droplet shape or aspect ratio, droplet size, proximity of the droplet to a second object or second droplet on the element array, and proximity of the droplet to a path of a second droplet moving along the array.

Another aspect of the invention is a related control method for controlling actuation voltages applied to array elements of an element array on an electro-wetting on dielectric (EWOD) device. In exemplary embodiments, the control method includes the steps of: receiving one or more fluid droplets on the element array; and applying a sequence of actuation voltages to a portion of the array elements associated with a droplet to maintain the droplet in a desired droplet state corresponding to a predetermined droplet property; wherein the sequence of actuation voltages includes an actuation-on period in which the portion of the array elements associated with the droplet is actuated and an actuation-off period in which the portion of the array elements associated with the droplet is not actuated, and the actuation-off period is non-zero. The microfluidic system may include one or more of the following features, either individually or in combination.

In an exemplary embodiment of the control method, applying a sequence of actuation voltages comprises applying actuation voltages in accordance with a predetermined duty cycle including a predetermined time, rate and duration of actuation voltages to the portion of the array elements associated with the droplet.

In an exemplary embodiment of the control method, the actuation-off period of the duty cycle is greater than the actuation-on period of the duty cycle.

In an exemplary embodiment of the control method, a ratio of the actuation-on period of the duty cycle to the actuation-off period of the duty cycle is less than or equal to 1:10.

In an exemplary embodiment of the control method, the duty cycle comprises applying actuation voltages to the array elements associated with a droplet for 0.5 seconds once every 5.0 seconds.

In an exemplary embodiment of the control method, the control method further includes: sensing a droplet state with a sensor; determining whether the sensed droplet state is a state that deviates from the desired droplet state in accordance with predetermined criteria; and applying actuation voltages to the portion of the array elements associated with the droplet when it is determined that the droplet state satisfies the predetermined criteria to return the droplet state to the desired droplet state.

In an exemplary embodiment of the control method, sensing a droplet state with the sensor comprises sensing a droplet position on the element array, the control method further comprising: determining whether the sensed droplet state is a state in which the droplet position deviates from a desired droplet state position in accordance with the predetermined criteria; and applying actuation voltages to the portion of the array elements associated with the droplet when it is determined that the droplet state satisfies the predetermined criteria to return the droplet state to the desired droplet state position.

In an exemplary embodiment of the control method, the predetermined criteria includes whether the droplet is at a position within a preset proximity to a second object on the element array.

In an exemplary embodiment of the control method, the predetermined criteria includes whether the droplet is at a position within a preset proximity to a path of a moving second droplet on the element array.

In an exemplary embodiment of the control method, sensing a droplet state with the sensor comprises sensing a droplet shape or aspect ratio, the control method further comprising: determining whether the sensed droplet state is a state in which the droplet shape or aspect ratio deviates from a desired droplet state shape or aspect ratio in accordance with predetermined criteria; and applying actuation voltages to the portion of the array elements associated with the droplet when it is determined that the droplet state satisfies the predetermined criteria to return the droplet state to the desired droplet state shape or aspect ratio.

In an exemplary embodiment of the control method, sensing a droplet state with the sensor comprises sensing a droplet size, the control method further comprising: determining whether the sensed droplet state is a state in which the droplet size deviates from a desired droplet state size in accordance with predetermined criteria; and applying actuation voltages to the portion of the array elements associated with the droplet when it is determined that the droplet state satisfies the predetermined criteria to return the droplet state to the desired droplet state size.

Another aspect of the invention is a non-transitory computer-readable medium storing program code which is executed by a processing device for controlling actuation voltages applied to array elements of an element array of an electro-wetting on dielectric (EWOD) device for performing droplet manipulations on droplets on the element array. The program code is executable by the processing device to perform the steps of the control method.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

The described embodiments could be used to provide an enhance AM-EWOD device. The AM-EWOD device could form a part of a lab-on-a-chip system. Such devices could be used in manipulating, reacting and sensing chemical, biochemical or physiological materials. Applications include healthcare diagnostic testing, material testing, chemical or biochemical material synthesis, proteomics, tools for research in life sciences and forensic science.

REFERENCE SIGNS LIST

10—lower substrate
12/12A.12B—element electrodes
14—liquid droplet
16—top substrate
18—spacer
20—non-polar surround fluid
22—insulator layer
24—first hydrophobic coating
26—contact angle
28—second hydrophobic coating
30—reference electrode
32—reader
34—cartridge
35—external sensor module
36—EWOD or AM-EWOD device
38—control electronics
40—storage device
42—cable of connecting wires
44—lower substrate
46—thin film electronics
48/48A/48B—element electrodes
50—electrode element array
51—array element
52—liquid droplet
54—top substrate
56—spacer
58—reference electrode
60—non-polar fluid
62—insulator layer
64—first hydrophobic coating
66—contact angle
68—second hydrophobic coating
70A—electrical load with droplet present
70B—electrical load without droplet present
72—array element circuit
74—row driver
76—column driver
78—sensor row addressing circuits
80—column detection circuits
82—serial interface
84—voltage supply interface
86—number of connecting wires
88—actuation circuit
90—sensor circuit
100—array of elements
102—individual array elements
102a—array elements associated with the droplet
102b—array elements not associated with the droplet
102c—array elements associated with a second droplet
104—droplet
106—second droplet

What is claimed is:

1. A microfluidic system comprising: an electro-wetting on dielectric (EWOD) device comprising an element array configured to receive one or more fluid droplets, the element array comprising a plurality of individual array elements; and
a control system configured to control actuation voltages applied to the element array to perform manipulation operations as to the fluid droplets;
wherein:
the control system is configured to apply a sequence of actuation voltages to a portion of the array elements comprising a plurality of array elements associated with a droplet, wherein the sequence of actuation voltages is applied commonly to the plurality of array elements to maintain the droplet in a desired droplet state corresponding to a predetermined droplet property; and
the sequence of actuation voltages includes an actuation-on period in which the plurality of array elements associated with the droplet commonly are actuated and an actuation-off period in which the plurality of array elements associated with the droplet commonly are not actuated, and the actuation-off period is non-zero.

2. The microfluidic system of claim 1, wherein the control system is configured to apply a sequence of actuation voltages comprising a predetermined duty cycle including a predetermined time, rate and duration of actuation voltages to the plurality of array elements associated with the droplet.

3. The microfluidic system of claim 2, wherein the actuation-off period of the duty cycle is greater than the actuation-on period of the duty cycle.

4. The microfluidic system of claim 2, wherein a ratio of the actuation-on period of the duty cycle to the actuation-off period of the duty cycle is less than or equal to 1:10.

5. The microfluidic system of claim 1, further comprising a sensor for sensing a droplet state,
and the control system is configured to:
receive droplet state information from the sensor;
determine whether a droplet is in a state that deviates from the desired droplet state in accordance with predetermined criteria based on the droplet state information; and
apply actuation voltages commonly to the plurality of array elements associated with the droplet when the control system determines that the droplet state satisfies the predetermined criteria to return the droplet to the desired droplet state.

6. The microfluidic system of claim 5, wherein the sensor comprises sensor circuitry incorporated into one or more array elements.

7. The microfluidic system of claim 1, wherein the predetermined droplet property of the desired droplet state is based on at least one of droplet position on the element array, droplet shape or aspect ratio, droplet size, proximity of the droplet to a second object or second droplet on the element array, and proximity of the droplet to a path of a second droplet moving along the array.

8. A control method for controlling actuation voltages applied to array elements of an element array on an electro-wetting on dielectric (EWOD) device, the control method comprising the steps of:
receiving one or more fluid droplets on the element array; and
applying a sequence of actuation voltages to a portion of the array elements comprising a plurality of array elements associated with a droplet, wherein the sequence of actuation voltages is applied commonly to the plurality of array elements to maintain the droplet in a desired droplet state corresponding to a predetermined droplet property; and
wherein the sequence of actuation voltages includes an actuation-on period in which the plurality of array elements associated with the droplet commonly are actuated and an actuation-off period in which the plurality of array elements associated with the droplet commonly are not actuated, and the actuation-off period is non-zero.

9. The control method of claim 8, wherein applying a sequence of actuation voltages comprises applying actuation voltages in accordance with a predetermined duty cycle including a predetermined time, rate and duration of actuation voltages to the portion of the array elements associated with the droplet.

10. The control method of 9, wherein the actuation-off period of the duty cycle is greater than the actuation-on period of the duty cycle.

11. The control method of claim 9, wherein a ratio of the actuation-on period of the duty cycle to the actuation-off period of the duty cycle is less than or equal to 1:10.

12. The control method of claim 9, wherein the duty cycle comprises applying actuation voltages to the array elements associated with a droplet for 0.5 seconds once every 5.0 seconds.

13. The control method of claim 8, further comprising:
sensing a droplet state with a sensor;
determining whether the sensed droplet state is a state that deviates from the desired droplet state in accordance with predetermined criteria; and
applying actuation voltages to the plurality of array elements associated with the droplet when it is determined that the droplet state satisfies the predetermined criteria to return the droplet state to the desired droplet state.

14. The control method of claim 13, wherein sensing a droplet state with the sensor comprises sensing a droplet position on the element array, the control method further comprising:
determining whether the sensed droplet state is a state in which the droplet position deviates from a desired droplet state position in accordance with the predetermined criteria; and
applying actuation voltages to the plurality of array elements associated with the droplet when it is determined that the droplet state satisfies the predetermined criteria to return the droplet state to the desired droplet state position.

15. The control method of claim 14, wherein the predetermined criteria includes whether the droplet is at a position within a preset proximity to a second object on the element array.

16. The control method of claim 14, wherein the predetermined criteria includes whether the droplet is at a position within a preset proximity to a path of a moving second droplet on the element array.

17. The control method of claim 13, wherein sensing a droplet state with the sensor comprises sensing a droplet shape or aspect ratio, the control method further comprising:
determining whether the sensed droplet state is a state in which the droplet shape or aspect ratio deviates from a desired droplet state shape or aspect ratio in accordance with predetermined criteria; and
applying actuation voltages to the plurality of array elements associated with the droplet when it is determined that the droplet state satisfies the predetermined criteria to return the droplet state to the desired droplet state shape or aspect ratio.

18. The control method of claim 13, wherein sensing a droplet state with the sensor comprises sensing a droplet size, the control method further comprising:
determining whether the sensed droplet state is a state in which the droplet size deviates from a desired droplet state size in accordance with predetermined criteria; and
applying actuation voltages to the plurality of array elements associated with the droplet when it is determined that the droplet state satisfies the predetermined criteria to return the droplet state to the desired droplet state size.

19. A non-transitory computer-readable medium storing program code which is executed a processing device for controlling actuation voltages applied to array elements of an element array of an electro-wetting on dielectric (EWOD) device for performing droplet manipulations on droplets on the element array, the program code being executable by the processing device to perform the steps of:
applying a sequence of actuation voltages to a portion of the array elements comprising a plurality of array elements associated with a droplet, wherein the sequence of actuation voltages is applied commonly to the plurality of array elements to maintain the droplet in a desired droplet state corresponding to a predetermined droplet property;
wherein the sequence of actuation voltages includes an actuation-on period in which the plurality of array elements associated with the droplet commonly are actuated and an actuation-off period in which the plurality of array elements associated with the droplet commonly are not actuated, and the actuation-off period is non-zero.

20. The non-transitory computer-readable medium of claim 19, wherein the program code is executable by the processing device further to perform the steps of:
sensing a droplet state by operation of a sensor;
determining whether the sensed droplet state is a state that deviates from the desired droplet state in accordance with predetermined criteria; and
applying actuation voltages to the plurality of array elements associated with the droplet when it is determined that the droplet state satisfies the predetermined criteria to return the droplet state to the desired droplet state.

* * * * *